(12) United States Patent
Thomas et al.

(10) Patent No.: US 6,291,455 B1
(45) Date of Patent: Sep. 18, 2001

(54) 4-ANILINOQUINAZOLINE DERIVATIVES

(75) Inventors: Andrew Peter Thomas; Craig Johnstone, both of Macclesfield (GB); Laurent Francois Andre Hennequin, Reims Cedex (FR)

(73) Assignees: Zeneca Limited, London (GB); Zeneca Pharma S.A., Cergy Cedex (FR)

(*) Notice: Subject to any disclaimer, the term of this patent is extended or adjusted under 35 U.S.C. 154(b) by 0 days.

(21) Appl. No.: 09/142,339

(22) PCT Filed: Feb. 28, 1997

(86) PCT No.: PCT/GB97/00550

§ 371 Date: Sep. 8, 1998

§ 102(e) Date: Sep. 8, 1998

(87) PCT Pub. No.: WO97/32856

PCT Pub. Date: Sep. 12, 1997

(30) Foreign Application Priority Data

Mar. 5, 1996 (EP) .................................. 96400468
Jul. 8, 1996 (EP) .................................. 96401499

(51) Int. Cl.[7] .................. A61K 31/517; A61P 29/00; A61P 35/00; C07D 239/94
(52) U.S. Cl. ................ 514/231.5; 514/259; 544/119; 544/293
(58) Field of Search ................ 514/259, 234.5, 514/231.5; 544/293, 119

(56) References Cited

U.S. PATENT DOCUMENTS

| | | | |
|---|---|---|---|
| 3,075,981 | 1/1963 | Surray et al. | 260/256.4 |
| 3,266,990 | 8/1966 | Lutz et al. | 167/65 |
| 3,272,824 | 9/1966 | Ebetino et al. | 260/288 |
| 3,755,332 | 8/1973 | Wasley et al. | 260/288 |
| 4,343,940 | 8/1982 | Kreighbaum et al. | 544/283 |
| 4,421,920 | 12/1983 | Baudouin et al. | 546/163 |
| 5,145,843 | 9/1992 | Arnold et al. | 546/163 |
| 5,409,930 | 4/1995 | Spada et al. | 544/353 |
| 5,457,105 | * 10/1995 | Barker | 544/293 |
| 5,480,883 | 1/1996 | Spada et al. | 544/353 |
| 5,506,235 | 4/1996 | Moyer et al. | 514/232.8 |
| 5,639,757 | 6/1997 | Dow et al. | 544/261 |
| 5,646,153 | 7/1997 | Spada et al. | 514/259 |
| 5,650,415 | 7/1997 | Tang et al. | 546/153 |
| 5,656,643 | 8/1997 | Spada et al. | 546/157 |
| 5,710,158 | 1/1998 | Myers et al. | 544/284 |
| 5,712,395 | 1/1998 | App et al. | 544/344 |
| 5,721,237 | 2/1998 | Myers et al. | 544/284 |
| 5,736,534 | 4/1998 | Arnold | 544/284 |
| 5,747,498 | 5/1998 | Schur et al. | 544/283 |
| 5,770,599 | 6/1998 | Gibson | 544/284 |
| 5,792,771 | * 9/1998 | App et al. | 544/293 |

FOREIGN PATENT DOCUMENTS

| | | |
|---|---|---|
| 02213558 | 10/1972 | (DE) . |
| 19521386 | 12/1996 | (DE) . |
| 19608588 | 9/1997 | (DE) . |
| 19608631 | 9/1997 | (DE) . |
| 19608653 | 9/1997 | (DE) . |
| 19614718 | 10/1997 | (DE) . |
| 19629652 | 1/1998 | (DE) . |
| 0 326 307 A2 | 2/1989 | (EP) . |
| 0 326 330 | 8/1989 | (EP) . |
| 0 520 722 | 12/1992 | (EP) . |
| 566 226 | 10/1993 | (EP) . |

(List continued on next page.)

OTHER PUBLICATIONS

Barlin et al., "Potential Antimalarials. XVIII Some Mono– and Di–Mannich Bases of 3–[7–Chloro(and trifluoromethyl)quinolin–4–ylamino]phenol", Aust. J. Chem., 1993, vol. 46, pp. 1685–1693.

(List continued on next page.)

*Primary Examiner*—Richard L. Raymond
*Assistant Examiner*—Venkataraman Balasubramanian
(74) *Attorney, Agent, or Firm*—Pillsbury Winthrop LLP

(57) ABSTRACT

The invention relates to quinazoline derivatives of formula (I) (wherein: $R^1$ represents hydrogen or methoxy; $R^2$ represents methoxy, ethoxy, 2-methoxyethoxy, 3-methoxypropoxy, 2-ethoxyethoxy, trifluoromethoxy, 2,2,2-trifluoroethoxy, 2-hydroxyethoxy, 3-hydroxypropoxy, 2-(N,N-dimethylamino)ethoxy, 3-(N,N-dimethylamino)propoxy, 2-morpholinoethoxy, 3-morpholinopropoxy, 4-morpholinobutoxy, 2-piperidinoethoxy, 3-piperidinopropoxy, 4-piperidinobutoxy, 2-(piperazin-1-yl)ethoxy, 3-(piperazin-1-yl)propoxy, 4-(piperazin-1-yl)butoxy, 2-(4-methylpiperazin-1-yl)ethoxy, 3-(4methylpiperazin-1-yl)propoxy or 4-(4-methylpiperazin-1-yl)butoxy; the phenyl group bearing $(R^3)_2$ is selected from: 2-fluoro-5-hydroxyphenyl, 4-bromo-2-fluorophenyl, 2,4-difluorophenyl, 4-chloro-2-fluorophenyl, 2-fluoro-4-methylphenyl, 2-fluoro-4-methoxyphenyl, 4-bromo-3-hydroxyphenyl, 4-fluoro-3-hydroxyphenyl, 4-chloro-3-hydroxyphenyl, 3-hydroxy-4-methylphenyl, 3-hydroxy-4-methoxyphenyl and 4-cyano-2-fluorophenyl); and salts thereof, processes for their preparation and pharmaceutical compositions containing a compound of formula (I) or a pharmaceutically acceptable salt thereof as active ingredient The compounds of formula (I) and the pharmaceutically acceptable salts thereof inhibit the effects of VEGF, a property of value in the treatment of a number of disease states including cancer and rheumatoid arthritis (I)

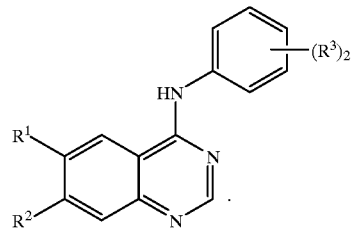

12 Claims, No Drawings

FOREIGN PATENT DOCUMENTS

| | | |
|---|---|---|
| 0 602 851 A1 | 6/1994 | (EP) . |
| 0 635 498 | 1/1995 | (EP) . |
| 0 635 507 A1 | 1/1995 | (EP) . |
| 0 682 027 A1 | 11/1995 | (EP) . |
| 0 743 308 | 11/1996 | (EP) . |
| 0 787 722 A1 | 8/1997 | (EP) . |
| 0 795 556 | 9/1997 | (EP) . |
| 0 837 063 A1 | 4/1998 | (EP) . |
| 2 077 455 | 10/1971 | (FR) . |
| 2 435 248 | 4/1980 | (FR) . |
| 2 033 894 | 5/1980 | (GB) . |
| 2 160 201 | 12/1985 | (GB) . |
| 43-20294 | 8/1943 | (JP) . |
| WO 86/06718 | 11/1986 | (WO) . |
| WO 87/04321 | 7/1987 | (WO) . |
| WO 92/14716 | 9/1992 | (WO) . |
| WO 92/16527 | 10/1992 | (WO) . |
| WO 95/06648 | 3/1995 | (WO) . |
| 95 15758 | 6/1995 | (WO) . |
| WO 95/15952 | 6/1995 | (WO) . |
| WO 95/19169 | 7/1995 | (WO) . |
| WO 95/19774 | 7/1995 | (WO) . |
| WO 95/19970 | 7/1995 | (WO) . |
| WO 95/21613 | 8/1995 | (WO) . |
| WO 95/23141 | 8/1995 | (WO) . |
| WO 95/24190 | 9/1995 | (WO) . |
| WO 96/07657 | 3/1996 | (WO) . |
| WO 96/09294 | 3/1996 | (WO) . |
| WO 96/15118 | 5/1996 | (WO) . |
| WO 96/16960 | 6/1996 | (WO) . |
| WO 96/29331 | 9/1996 | (WO) . |
| 96 33977 | 10/1996 | (WO) . |
| WO 96/30347 | 10/1996 | (WO) . |
| WO 96/30370 | 10/1996 | (WO) . |
| WO 96/31510 | 10/1996 | (WO) . |
| WO 96/33978 | 10/1996 | (WO) . |
| WO 96/33979 | 10/1996 | (WO) . |
| WO 96/33980 | 10/1996 | (WO) . |
| WO 96/33981 | 10/1996 | (WO) . |
| WO 96-34867 | 11/1996 | (WO) . |
| WO 96/35689 | 11/1996 | (WO) . |
| WO 96/39145 | 12/1996 | (WO) . |
| WO 96/40142 | 12/1996 | (WO) . |
| WO 96/40648 | 12/1996 | (WO) . |
| WO 97/02266 | 1/1997 | (WO) . |
| WO 97/03069 | 1/1997 | (WO) . |
| WO 97/13760 | 4/1997 | (WO) . |
| WO 97/13771 | 4/1997 | (WO) . |
| WO 97/14691 | 4/1997 | (WO) . |
| WO 97/16435 | 5/1997 | (WO) . |
| WO 97/17329 | 5/1997 | (WO) . |
| WO 97/18212 | 5/1997 | (WO) . |
| WO 97/22596 | 6/1997 | (WO) . |
| WO 97/28161 | 8/1997 | (WO) . |
| WO 97/30034 | 8/1997 | (WO) . |
| WO 9730044 | 8/1997 | (WO) . |
| WO 97/30035 | 9/1997 | (WO) . |
| WO 97/37999 | 10/1997 | (WO) . |
| WO 97/38983 | 10/1997 | (WO) . |
| WO 97/38994 | 10/1997 | (WO) . |
| WO 97/49688 | 12/1997 | (WO) . |
| WO 97/49689 | 12/1997 | (WO) . |
| WO 98/02434 | 1/1998 | (WO) . |
| WO 98/02437 | 1/1998 | (WO) . |
| WO 98/02438 | 1/1998 | (WO) . |
| WO 98/07726 | 2/1998 | (WO) . |
| WO 98/10767 | 3/1998 | (WO) . |
| WO 98/14431 | 4/1998 | (WO) . |
| WO 98/23613 | 6/1998 | (WO) . |

OTHER PUBLICATIONS

Barlin et al., "Potential Antimalarials. XX Mannich Base Derivatives 2–(7–trifluoromethylquinolin–4–ylamino)phenol", Aust. J. Chem, 1994, vol. 47, pp. 1143,–1154.

Galanakis et al., "Synthesis and Quantitative Structure . . . Substituent of Position 4 of the Quinoline Ring", J. Med. Chem. 1995, vol. 38, pp. 3536–3546.

Hester, "Heterocyclic Synthesis Based on the Reactions of Dimethyl Acetylenedicarboxylate with the 2–Amino–5–chlorobenzophenone Oximes", Journal of Organic Chemistry, Jul. 1974, vol. 39, No. 15, pp. 2137–2142.

lfe et al., "Reversible Inhibitors of the Gastric ($H^+/K^+$) ATPase. 3. 3–Substituted–4–(phenylamino)quinolines", J. Med. Chem., 1992, vol. 35, pp. 3413–3422.

Lin et al., "Some Physiocochemical Parameters of 11H–Indolo[3,2–c]Quinoline", Heterocycles, 1989, vol. 29, No. 12, pp. 2353–2359.

Moyer et al., "The Synthesis and Identification of 4–6, Diaminoquinoline Derivatives as Potent Immunostimulants", Bioorganic ahd Medicinal Chimistry Letters, 1992, vol., 2, No. 12, pp. 1589–1594.

Yamamoto et al., "Reaction of Carbondiimide with Aldehyde", J. Org. Chem., 1974, vol. 39, No. 24, pp. 3516–3519.

Klagsbrun, M., and D'Amore, P.A. Vascular Endothelial Growth Factor and its Receptors. Cytokine & Growth Factors Reviews, vol. 7, pp. 259–270, Oct. 1996.*

Arya et al., Nitroimidazoles: Part XVI—Some 1–Methyl–4–nitro–5–substituted Imidazoles, Indian Journal of Chemistry, vol. 21B, Dec. 1982, pp. 1115–1117.

Bridges, "The current status of tyrosine kinase inhibitors . . . ," Exp.Opin.Ther.Patents (1995), 5(12): 1245–1257, Editorial, Oncologic, Endocrine & Metabolic, 1995 Ashley Publications Ltd ISSN 1354–3776.

Bridges, et al., "Enantioselective Inhibition of the Epidermal Growth Factor Receptor Tyrosine Kinase by 4–(a–Phenethylamino)quinazolines," Bioorganic & Medicinal Chemistry, vol. 3, No. 12, pp. 1651–1656, 1995.

Buchdunger, et al., "4,5–Dianilinophthalimide: A proteintyrosine kinase inhibitor with selectivity for the epidermal growth factor . . . ," Proc.Natl.Acad.Sci., USA, vol. 91, pp. 2334–2338, Mar. 1994, Applied Biological Sciences.

Burke, Jr., "Protein–tyrosine kinase inhibitors," Drugs of the Future 1992, vol. 17(2), pp. 119–131.

Connolly, et al., "Human Vascular Permeability Factor," J.Bio.Chem., vol. 264, No. 33, Nov. 1989, pp. 20017–20024.

Cullinan–Bove, et al., "Vascular Endothelial Growth Factor/Vascular Permeability Factor Expression in the Rat Uterus . . . ," Endocrinology, vol. 133, No. 2, 1993, pp. 829–837.

Dolle, et al., "5,7–Dimethoxy–3–(4–pyridinyl)quinoline Is a Potent and Selective Inhibitor of Human Vascular b–Type Platelet–Derived Growth Factor Receptor Tyrosine Kinase," J.Med.Chem. 1994, vol. 37, pp. 2627–2629.

Fan, et al., "Controlling the Vasculature: Angiogenesis, Anti–Angiogenesis . . . ," TiPS Review, vol. 16, Feb. 1995, pp. 57–65.

Folkman, "Angiogenesis in Cancer, Vascular, Rheumatoid and Other Disease," Nature Medicine, vol. 1, No. 1, 1995, pp. 27–30.

Fry et al., "A Specific Inhibitor of the Epidermal Growth Factor Receptor Tyrosine Kinase," Science, vol. 265, Aug. 19, 1994, pp. 1093–1095.

Gazit et al., Tyrophostins IV–Highly Potent Inhibitors . . . Relationship Study of 4–Anilidoquinazolines, Bioorganic & Medicinal Chemistry, vol. 4, No. 8, 1996, pp. 1203–1207.

Golovkin et al., *Nauchin TR–VSES–NAUCHNO–ISSLED INST FARM*, 1990, 28, 70–75.

Hara et al., On the Amination of Azaheterocycles. A New Procedure for the Introduction of an Amino Group (1), J. Heterocyclic Chem. vol. 19, 1982, pp. 1285–1287.

Higashino et al., Reactions of the Anion Reissert Compound . . . with Electrophiles, Chem. Pharm. Bull., vol. 33(3), 1985, pp. 950–961.

Iyer, et al., "Studies in Potential Amoebicides: Part III—Synthesis of 4–Substituted Amino 8–Hydroxy) Quinazolines & 3–Substituted 8–Hydroxy(&8–Methoxy)–4–Quinazolones," J.Sci.Industr.Res., vol. 15C, Jan. 1956, pp. 1–7.

Jakeman, et al., "Developmental Expression of Binding Sites and Messenger Ribonucleic Acid . . . ," Endocrinology, vol. 133, No. 2, 1993, pp. 848–859.

Karminski et al., The Synthesis of Some Quinazoline Derivatives and Their Biological Properties; J. Environ. Sci. Health, vol. B18, 1983, pp. 599–610.

Kim, et al., "Inhibition of Vascular Endothelial Growth Factor–Induced Angiogenesis Suppresses Tumour Growth in Vivo," Nature, vol. 362, Apr. 1993, pp. 841–844.

Kobayashi, Derwent Abstract 82–87077, vol. 6, No. 244, Dec. 1982, JP 57–144266, Sep. 1982, "4–Anilinoquinazoline Derivative, its Preparation and Analgesic and Antiphlogistic Agent Containing Said Derivative as Active Component". (n.7).

Kolch, et al., "Regulation of the Expression of the VEGF/VPS and its Receptors: Role in Tumor Angiogenesis," Breast Cancer Research and Treatment, vol. 36, 1995, pp. 139–155.

Kumar et al., Reactions of Diazines with Nucleophiles—IV.1 The Reactivity . . . Single Electron Transfer Reactions, Bioorganic & Medicinal Chemistry, vol. 3, No. 7, 1995, pp. 891–897.

Kyorin, Derwent Abstract 84–53835, JP 59–13765, Jan. 1984, "2–(4–Quinazolinyl)amino benzoic acid derivs . . . having analgesic and antiinflammatory activities". (n.8).

Li, et al., Chem.Abs., vol. 92:76445u, 1980, pp. 674–675.

Lin et al., Chem.Abs., vol. 96:122728w, 1982, p. 695.

Maguire, et al., "A New Series of PDGF Receptor Tyrosine Kinase Inhibitors: 3–Substituted Quinoline Derivatives," J.Med.Chem. 1994, vol. 37, pp. 2129–2137.

Nagarajan et al., Nitroimidazoles: Part XIX†—Structure Activity Relationships‡, Indian Journal of Chemistry, vol. 23B, Apr. 1984, pp. 342–362.

Nomoto et al., Studies on Cardiotonic Agents. VII.1) Potent Cardiotonic Agent KF15232 with Myofibrillar CA2+ Sensitizing Effect, Chem. Pharm. Bull., vol. 39(4), 1991, pp. 900–910.

Rewcastle et al., "Tyrosine Kinase Inhibitors. 5 . . . 4–(Phenylamino)quinazolines as Potent . . . Inhibitors of the Tyrosine Kinase Domain of the Epidermal Growth Factor Receptor," J.Med.Chem. 1995, vol. 38, pp. 3482–3487.

Sankyo and Ube, Derwent Abstract 81–28290, JP 56–20577, Feb. 1981, "4–(N–alkyl:anilino) quinazoline derivs . . . having analgesic and antiinflammatory actions". (n.9).

Schonowsky et al., Chinazolinderivate, ihre Herstellung und biologische Wirkung, Quinzaolines, their Preparation and Biological Activity, Z. Naturforsch, 37b, 1982, pp. 907–911.

Senger, et al., "Vascular Permeability Factor (VPF, VEGF) in Tumor Biology," Cancer and Metastasis Reviews, vol. 12, 1993, pp. 303–324.

Sinyak, et al., Synthesis and Biological Properties of Derivatives of 4–Heterylmercaptoquinazoline, Zaporozh'e Medical Institute pp. 103–106, translated from Khimiko–farmatsevticheskii Zhurnal, vol. 20, No. 2, Feb. 1986, 168–171, original article submitted Dec. 29, 1984.

Spada, et al., Small molecule inhibitors of tyrosine Kinase activity, Exp.Opin.Ther.Patents (1995), 5(8):805–817, Patent Update, Oncologic, Endocrine & Metabolic, Ashley Publications Ltd ISSN 1354–3776.

Spence, "Inhibitors of Tyrosine Kinase Activity as Anticancer Therapeutics: Recent Developments," Expert Opinion in Therapeutic Patents, Jan. 1993, Patent Update, Anticancers, etc., pp. 3–9, Current Drugs Ltd ISSN 0962–2594.

Stets et al., Investigation of Anti–Arrhythmic Action of Quinazopyrine, Pharmacology Dept., Zaporozhye Medical Institute, Zaporozhye, and Vinnitsa Medical Institute, Vinnitsa, pp. 94–96, translated from Farmakol. 1 toksik., vol. 53, No. 3, 1990, pp. 15–17.

Traxler, et al., "Recent advances in protein tyrosine kinase inhibitors," Drugs of the Future 1995, vol. 20(12, pp. 1261–1274.

Trinks, et al., "Dianilinophthalimides: Potent and Selective, ATP–Competitive Inhibitors of the EGF–Receptor Protein Tyrosine Kinase," J.Med. Chem. 1994, vol. 37, pp. 1015–1027.

Vinogradoff et a;/, Development of a New Synthesis of . . . Sodium Salt via an Amidine Intermediate, J. Heterocyclic Chem. vol. 26, 97, Jan.–Feb. 1989, pp. 97–103.

Ward, et al., "Epidermal Growth Factor Receptor Tyrosine Kinase—Investigation of Catalytic Mechanism, Structure-Based Searching and Discovery of a Potent Inhibitor," Biochem.Pharmacology, vol. 48, No. 4, pp. 659–666 (1994).

Wolfe et al., A Facile One–Step Synthesis of Certain 4-(4–Pyrimidinylmethyl)quinazolines, J. Heterocyclic Chem., vol. 13, 1976, pp. 383–385.

* cited by examiner

4-ANILINOQUINAZOLINE DERIVATIVES

This application is the national phase of international application PCT/GB97/00550 filed Feb. 28, 1997 which designated the U.S.

The present invention relates to quinazoline derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Alteration of vascular permeability is thought to play a role in both normal and pathological physiological processes (Cullinan-Bove et al, 1993, Endocrinology 133: 829–837; Senger et al, 199:3, Cancer and Metastasis Reviews, 12: 303–324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36:139–155) and vascular permeability (Connolly et al, 1989, J. Biol. Chem. 264: 20017–20024). Antagonism of VEGF action by sequestration of VEGF with antibody can result in inhibition of tumour growth (Kim et al, 1993, Nature 362: 841–844).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain. Binding of ligand. to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 989–991; Terman et al, 1992, Biochem. Biophys. Res. Comm. 1992, 187: 1579–1586). Binding of VEGF to these receptors expressed in heterologous c ells has been associated with changes in the tyrosine phosphorylation status of cellular proteins and calcium fluxes.

European Patent Publication No. 0326330 discloses certain quinoline, quinazoline and cinnoline plant fungicides. Certain of these plant fungicides are also stated to possess insecticidal and miticidal activity. There is however no disclosure or any suggestion that any of the compounds disclosed may be used for any purpose in animals such as humans. In particular, the European Patent Publication contains no teaching whatsoever concerning angiogenesis and/or increased vascular permeability mediated by growth factors such as VEGF.

European Patent Publication No. 0566226 describes compounds having activity against epidermal growth factor (EGF) receptor tyrosine kinase. Whilst the compounds of the present invention fall within the broad general disclosure of EP 0566226, we have found, surprisingly, that the compounds of the present invention possess very good inhibitory activity against VEGF, a property nowhere disclosed in EP 0566226. Moreover compounds of EP 0566226, outside the scope of the present invention, which have been tested, do not show significant inhibtory activity against VEGF receptor tyrosine kinase.

The present invention is thus based on the discovery of compounds that surprisingly inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. Compounds of the present invention possess higher potency against VEGF receptor tyrosine kinase whilst possessing some activity against EGF receptor tyrosine kinase. Furthermore, compounds of the present invention, possess substantially higher potency against VEGF receptor tyrosine kinase than against EGF receptor tyrosine kinase or FGF R1 receptor tyrosine kinase.

According to one aspect of the present invention there is provided a quinazoline derivative of the formula I:

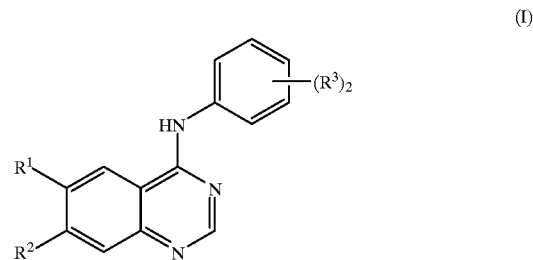

(wherein:
$R^1$ represents hydrogen or methoxy;
$R^2$ represents methoxy, ethoxy, 2-methoxyethoxy, 3-methoxypropoxy, 2-ethoxyethoxy, trifluoromethoxy, 2,2,2-trifluoroethoxy, 2-hydroxyethoxy, 3-hydroxypropoxy, 2-(N,N-dimethylamino)ethoxy, 3-(N,N-dimethylamino)propoxy, 2-morpholinoethoxy, 3-morpholinopropoxy, 4-morpholinobutoxy, 2-piperidinoethoxy, 3-piperidinopropoxy, 4-piperidinobutoxy, 2-(piperazin-1-yl)ethoxy, 3-(piperazin-1-yl)propoxy, 4-(piperazin-1-yl)butoxy, 2-(4-methylpiperazin-1-yl)ethoxy, 3-(4-methylpiperazin-1-yl)propoxy or 4-(4-methylpiperazin-1-yl)butoxy;
the phenyl group beaming $(R^3)_2$ is selected from: 2-fluoro-5-hydroxyphenyl, 4-bromo-2-fluorophenyl, 2,4-difluorophenyl, 4-chloro-2-fluorophenyl, 2-fluoro-4-methylphenyl, 2-fluoro-4-methoxyphenyl, 4-bromo-3- hydroxyphenyl, 4-fluoro-3-hydroxyphenyl, 4-chloro-3-hydroxyphenyl, 3-hydroxy-4-methylphenyl, 3-hydroxy-4-methoxyphenyl and 4-cyano-2-fluorophenyl);
and salts thereof.

$R^1$ is preferably methoxy.

Advantageously $R^2$ represents methoxy, ethoxy, 2-methoxyethoxy, 3-methoxypropoxy, trifluoromethoxy, 2,2,2-trifuoroethoxy, 2-hydroxyethoxy, 3-hydroxypropoxy, 2-(N,N-dimethylamino)ethoxy, 3-(N,N-dimethylamino)propoxy, 2-morpholinoethoxy, 3-morpholinopropoxy, 2-piperidinoethoxy, 3-piperidinopropoxy, 2-(piperazin-1-yl)ethoxy or 3-(piperazin-1-yl)propoxy. Further advantageous values of $R^2$ are 2-($^4$-methylpiperain-1-yl)ethoxy and 3-(4-methylpiperazin-1-yl)propoxy.

Preferably $R^2$ is methoxy, ethoxy, 2-methoxyethoxy, 3-methoxypropoxy, 2,2,2-trifluoroethoxy, 2-hydroxyethoxy, 3-hydroxypropoxy, 2-(N,N-dimethylamino)ethoxy, 3-(N,N-dimethylamino)propoxy, 2-morpholinoethoxy, 3-morpholinopropoxy, 2-piperidinoethoxy, 3-piperidinopropoxy, 2-(piperazin-1-yl)ethoxy or 3-(piperazin-1-yl)propoxy. Additional preferred values of $R^2$ are 2-(4-methylpiperazin-1-yl)ethoxy and 3-(4-methylpiperazin-1-yl)propoxy.

More preferably $R^2$ is 2-methoxyethoxy, 2-hydroxyethoxy, 3-(N,N-dimethylamino)propoxy, 2-morpholinoethoxy, 3-morpholinopropoxy or 3-(piperazin-1-yl)propoxy, and additional more preferred values of $R^2$ are 2-(4-methylpiperazin-1-yl)ethoxy and 3-(4-methylpiperazin-1-yl)propoxy.

Particularly preferred values of $R^2$ are 2-methoxyethoxy, 2-morpholinoethoxy, 3-morpholinopropoxy and 2-(4-methylpiperazin-1-yl)ethoxy.

Especially preferred values of $R^2$ are 2-methoxyethoxy and 3-morpholinopropoxy.

In a particular aspect of the invention the phenyl group bearing $(R^3)_2$ is selected from: 2-fluoro-5-hydroxyphenyl, 4-bromo-2-fluorophenyl, 2,4-difluorophenyl, 4-chloro-2-fluorophenyl, 2-fluoro-4-methylphenyl, 2-fluoro-4-methoxyphenyl, 4-bromo-3-hydroxyphenyl, 4-fluoro-3-hydroxyphenyl, 4-chloro-3-hydroxyphenyl, 3-hydroxy-4-methylphenyl and 3-hydroxy-4-methoxyphenyl.

The phenyl group bearing $(R^3)_2$ is preferably 3-hydroxy-4-methylphenyl or 4-chloro-2-fluorophenyl especially 4-chloro-2-fluorophenyl. A further especially preferred value for the phenyl group bearing $(R^3)_2$ is 4-bromo-2-fluorophenyl.

Preferred compounds are
4-(4-chloro-2-fluoroanilino)-7-(2-methoxyethoxy)quinazoline,
6,7-dimethoxy-4-(2-fluoro-5-hyidroxyanilino)quinazoline,
4-(4-chloro-3-hydroxyanilino)-6,7-dimethoxyquinazoline,
4-(4-chloro-2-fluoroanilino)-6-methoxy-7-(2-methoxyethoxy)quinazoline,
4-(4-chloro-2-fluoroanilino)-6,7-dimethoxyquinazoline,
4-(3-hydroxy-4-methylamino)-6-methoxy-7-(3-morpholinopropoxy)quinazoline,
4-(4-chloro-2-fluoroanilino)-7-(3-hydroxypropoxy)-6-methoxyquinazoline,
4-(4-chloro-2-fluoroanilino)-6-methoxy-7-(2-morpholinoethoxy)quinazoline,
4-(4-chloro-2-fluoroanilino)-6-methoxy-7-(3-morpholinopropoxy)quinazoline,
4-(3-hydroxy-4-methylanilino)-6-methoxy-7-(2-methoxyethoxy)quinazoline
and salts thereof especially hydrochloride salts thereof,
and other preferred compounds are
10 4-(4-bromo-2-fluoroanilino)-6,7-dimethoxyquinazoline,
4-(2-fluoro-4-methylanilino)-.6,7-dimethoxyquinazoline,
6,7-dimethoxy-4-(3 hydroxy-4-methylanilino)quinazoline,
4-(4-bromo-2-fluoroanilino)-6-methoxy-7-(2-methoxyethoxy)quinazoline,
4-(2-fluoro-4-methylanilino)-65-methoxy-7-(2-methoxyethoxy)quinazoline,
4-(3-hydroxy-4-methylanilino)-7-(2-methoxyethoxy)quinazoline,
4-(4-chloro-2-fluoroanilino)-6-methoxy-7-(2-(4-methylpiperazin-1-yl)ethoxy)quinazoline,
4-(4-bromo-2-fluoroanilino)-6-methoxy-7-(3-morpholinopropoxy)quinazoline,
4-(4-chloro-2-fluoroanilino)-7-(3-morpholinopropoxy)quinazoline,
4-(4-cyano-2-fluoroanilino)-6-methoxy-7-(3-morpholinopropoxy)quinazoline,
4-(4-chloro-2-fluoroanilino)-6-methoxy-7-(3-methoxypropoxy)quinazoline,
4-(4-chloro-2-fluoroanilino)-6-methoxy-7-(2-ethoxyethoxy)quinazoline,
4-(4-chloro-2-fluoroanilino)-7-(2-hydroxyethoxy)-6-methoxyquinazoline,
4-(4-bromo-2-fluoroanilino)-6-methoxy-7-(2-(4-methylpiperazin-1-yl)ethoxy)quinazoline,
4-(4-bromo-2-fluoroanilino)-6-methoxy-7-(2-morpholinoethoxy)quinazoline,
4-(4-chloro-2-fluoroanilino)-6-methoxy-7-(4-morpholinobutoxy)quinazoline,
4-(4-chloro-2-fluoroanilino)-6-methoxy-7-(3-(4-methylpiperazin-1yl)propoxy)quinazoline
and salts thereof especially hydrochloride salts thereof.
More preferred compounds are
4-(4-chloro-2-fluoroanilino)-7-(2-methoxyethoxy)quinazoline,
4-($^4$-chloro-2-fluoroanilino)-6-methoxy-7-(2-methoxyethoxy)quinazoline,
4-(4-chloro-2-fluoroanilino)-6,7-dimethoxyquinazoline,
4-(3-hydroxy-4-methylanilino)-6-methoxy-7-(3-morpholinopropoxy)quinazoline,
4-(4-chloro-2-fluoroanilino)-7-(3-hydroxypropoxy)-6-methoxyquinazoline,
4-(4-chloro-2-fluoroanilino)-6-methoxy-7-(2-morpholinoethoxy)quinazoline,
4-(4-chloro-2-fluoroanilino)-6-methoxy-7-(3-morpholinopropoxy)quinazoline,
4-(3-hydroxy-4-methylanilino)-6-methoxy-7-(2-methoxyethoxy)quinazoline,
4-(4-bromo-2-fluoroanilino)-6-methoxy-7-(2-methoxyethoxy)quinazoline,
4-(2-fluoro-4-methylanilino)-6-methoxy-7-(2-methoxyethoxy)quinazoline,
4-(3-hydroxy-4-methylanilino)-7-(2-methoxyethoxy)quinazoline,
4-(4-chloro-2-fluoroanilino)-6-methoxy-7-(2-(4-methylpiperazin-1-yl)ethoxy)quinazoline,
4-(4-bromo-2-fluoroanilino)-6-methoxy-7-(3-morpholinopropoxy)quinazoline,
4-(4-chloro-2-fluoroanilino)-7-(3-morpholinopropoxy)quinazoline,
4-(4-cyano-2-fluoroanilino)-6-methoxy-7-(3-morpholinopropoxy)quinazoline,
4-(4-chloro-2-fuoroanilino)-6-methoxy-7-(3-methoxypropoxy)quinazoline,
4-(4-chloro-2-fluoroanilino)-6-methoxy-7-(2-ethoxyethoxy)quinazoline,
4-(4-chloro-2-fluoroanilino)-7-(2-hydroxyethoxy)-6-methoxyquinazoline, 4-(4-bromo-2-fluoroanilino)-6-methoxy-7-(2-(4-methylpiperazin-1-yl)ethoxy)quinazoline,
4-(4-bromo-2-fluoroanilino)-6-methoxy-7-(2-morpholinoethoxy)quinazoline,
4-(4-chloro-2-fluoroanilino)-6-methoxy-7-(4-morpholinobutoxy)quinazoline,
4-(4-chloro-2-fluoroanilino)-6-methoxy-7-(3-(4-methylpiperazin-1-yl)propoxy)quinazoline and salts thereof especially hydrochloride salts thereof.
Particularly preferred compounds are
4-(4-chloro-2-fluoroanilino)-7-(2-methoxyethoxy)quinazoline,
4-(4-chloro-2-fluoroanilino)-6-methoxy-7-(2-methoxyethoxy)quinazoline,
4-(4-chloro-2-fluoroanilino)-6,7-dimethoxyquinazoline,
4-(4-chloro-2-fluoroanilino)-7-(3-hydroxypropoxy)-6-methoxyquinazoline,
4-(4-chloro-2-fluoroanilino)-6-methoxy-7-(2-morpholinoethoxy)quinazoline,
4-(4-chloro-2-fluoroanilino)-6-methoxy-7-(3-morpholinopropoxy)quinazoline and salts thereof especially hydrochloride salts thereof, other particularly preferred compounds are
4-(4-bromo-2-fluoroanilino)-6-methoxy-7-(2-methoxyethoxy)quinazoline.
4-(4-chloro-2-fluoroanilino)-6-methoxy-7-(2-(4-methylpiperazin-1-yl)ethoxy)quinazoline,
4-(4-bromo-2-fluoroanilino)6-methoxy-7-(3-morpholinopropoxy)quinazoline,
4-(4-bromo-2-fluoroanilino)-6-methoxy-7-(2-(4-methylpiperazin-1-yl)ethoxy)quinazoline,
4-(4-bromo-2-fluoroanilino)-6-methoxy-7-(2-morpholinoethoxy)quinazoline and salts thereof especially hydrochloride salts thereof.
More particularly preferred compounds are
4-(4-chloro-2-fluoroanilino)-7-(2-methoxyethoxy)quinazoline,
4-(4-chloro-2-fluoroanilino)-6-methoxy-7-(2-methoxyethoxy)quinazoline,
4-(4-chloro-2-fluoroanilino)-7-(3-hydroxypropoxy)-6-methoxyquinazoline,
4-(4-chloro-2-fluoroanilino)-6-methoxy-7-(2-morpholinoethoxy)quinazoline,
4-(4-chloro-2-fluoroanilino)-6-methoxy-7-(3-morpholinopropoxy)quinazoline,
4-(4-bromo-2-fluoroanilino)-6-methoxy-7-(2-methoxyethoxy)quinazoline,
4-(4-chloro-2-fluoroanilino)-6-methoxy-7-(2-(4-methylpiperazin-1-yl)ethoxy)quinazoline,
4-(4-bromo-2-fluoroanilino)-6-methoxy-7-(3-morpholinopropoxy)quinazoline,
4-(4-bromo-2-fluoroanilino)-6-methoxy-7-(2-(4-methylpiperazin-1-yl)ethoxy)quinazoline,
4-(4-bromo-2-fluoroanilino)-6-methoxy-7-(2-morpholinoethoxy)quinazoline and salts thereof especially hydrochloride salts thereof.
Especially preferred compounds are
4-(4-chloro-2-fluoroanilino)-6-methoxy-7-(2-methoxyethoxy)quinazoline,
4-(4-chloro-2-fluoroanilino)-6-methoxy-7-(2-morpholinoethoxy)quinazoline,
4(4-chloro-2-fluoroanilino)-6-methoxy-7-(3-morpholinopropoxy)quinazoline,
4-(4-bromo-2-fluoroanilino)-6-methoxy-7-(2-methoxyethoxy)quinazoline.
4-(4-chloro-2-fluoroanilino)-6-methoxy-7-(2-(4-methylpiperazin-1-yl)ethoxy)quinazoline,
4-(4-bromo-2-fluoroanilino)-6-methoxy-7-(3-morpholinopropoxy)quinazoline,
4-(4-bromo-2-fluoroanilino)-6-methoxy-7-(2-(4-methylpiperazin-1-yl)ethoxy)quinazoline,
4-(4-bromo-2-fluoroanilino)-6-methoxy-7-(2-morpholinoethoxy)quinazoline and salts thereof especially hydrochloride salts thereof.
More especially preferred compounds are
4-(4-chloro-2-fluoroanilino)-6-methoxy-7-(2-methoxyethoxy)quinazoline,
4-(4-chloro-2-fluoroanilino)-6-methoxy-7-(3-morpholinopropoxy)quinazoline,
4-(4-chloro-2-fluoroanilino)-6-methoxy-7-(2-morpholinoethoxy)quinazoline,
4-(4-chloro-2-fluoroanilino)-6-methoxy-7-(2-(4-methylpiperazin-1-yl)ethoxy)quinazoline,
4-(4-bromo-2-fluoroanilino)-6-methoxy-7-(3-morpholinopropoxy)quinazoline and salts thereof especially hydrochloride salts thereof, of which
4-(4-chloro-2-fluoroanilino)-6-methoxy-7-(2-methoxyethoxy)quinazoline,
4-(4-chloro-2-fluoroanilino)-6-methoxy-7-(3-morpholinopropoxy)quinazoline and salts thereof especially hydrochloride salts thereof are preferred.

For the avoidance of doubt it is to be understood that where in this specification a group is qualified by 'hereinbefore defined' or 'defined hereinbefore' the said group encompasses the first occurring and broadest definition as well as each and all of the preferred definitions for that group.

In this specification the term "alkyl" includes both straight and branched chain alkyl groups but references to individual alkyl groups such as "propyl" are specific for the straight chain version only. An analogous convention applies to other generic terms. Unless otherwise stated the term "alkyl" advantageously refers to chains with 1–6 carbon atoms, preferably 1–4 carbon atoms.

In this specification the term "alkoxy" means an alkyl group as defined hereinbefore linked to an oxygen atom.

In this specification the term "aryl" includes $C_{6-10}$ aromatic groups which may, if desired, carry one or more substituents selected from halogeno, alkyl, alkoxy, cyano, nitro or trifluoromethyl (wherein alkyl and alkoxy are as hereinbefore defined). The term "aryloxy" means an aryl group as defined hereinbefore linked to an oxygen atom.

In this specification the term "sulphonyloxy" includes alkylsulphonyloxy and arylsulphonyloxy wherein "alkyl" and "aryl" are as defined hereinbefore.

In formula I, as hereirnbefore defined, hydrogen will be present at positions 2, 5 and 8 of the quinazoline group.

Within the present invention it is to be understood that a quinazoline of the formula I or a salt thereof may exhibit the phenomenon of tautomerism and that the formulae drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings.

It is also to be understood that certain quinazolines of the formula I and salts thereof can exist in solvated as well as unsolvated forms such as, for example, hydrated forms. It is to be understood that the invention encompasses all such solvated forms which inhibit VEGF receptor tyrosine kinase activity.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

A compound of the formula I, or salt thereof, and other compounds of the invention (as hereinafter defined) may be prepared by any process known to be applicable to the preparation of chemically-related compounds. Such processes include, for example, those illustrated in European Patent Applications, Publication Nos. 0520722, 0566226. 0602851 and 0635498. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus the following processes (a) to (e) and (i) to (v) constitute further features of the present invention.
Synthesis of Compounds of Formula I (a) Compounds of the formula I and salts thereof may be prepared by the reaction of a compound of the formula III:

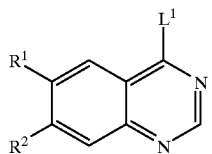

(III)

(wherein $R^1$ and $R^2$ are as defined hereinbefore and $L^1$ is a displaceable moiety), with a compound of the formula IV:

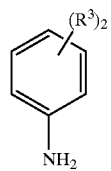

(IV)

(wherein $R^3$ is as defined hereinbefore) whereby to obtain compounds of the formula I and salts thereof. A convenient displaceable moiety $L^1$ is, for example, a halogeno, alkoxy (preferably $C_{1-4}$alkoxy), aryloxy or sulphonyloxy group, for example a chloro, bromo, methoxy, phenoxy, methanesulphonyloxy or toluene-4-sulphonyloxy group.

The reaction is advantageously effected in the presence of either an acid or a base. Such an acid is, for example, an anhydrous inorganic acid such as hydrogen chloride. Such a base is, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or for example, an alkali metal or alkaline earth metal carbonate or hydroxide, for example sodium carbonate, potassium carbonate, calcium carbonate, sodium hydroxide or potassium hydroxide. Alternatively such a base is, for example, an alkali metal hydride, for example sodium hydride, or an alkali metal or alkaline earth metal amide, for example sodium amide or sodium bis(trimethylsilyl)amide. The reaction is preferably effected in the presence of an inert solvent or diluent, for example an alkanol or ester such as methanol, ethanol, isopropanol or ethyl acetate, a halogenated solvent such as methylene chloride, trichloromethane or carbon tetrachloride, an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethylsulphoxide. The reaction is conveniently effected at a temperature in the range, for example, 10 to 150° C., preferably in the range 20 to 80° C.

The compound of the invention may be obtained from this process in the form of the free base or alternatively it may be obtained in the form of a salt with the acid of the formula H-L' wherein $L^1$ has the meaning defined hereinbefore. When it is desired to obtain the free base from the salt, the salt may be treated with a base as defined hereinbefore using a conventional procedure.

(b) Where the group of formula II:

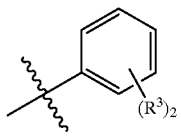

(II)

(wherein $R^3$ is as hereinbefore defined) represents a phenyl group carrying a hydroxy group, a compound of the formula I and salts thereof can be prepared by the deprotection of a compound of formula V:

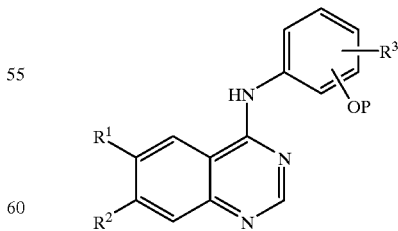

(V)

(wherein $R^1$, $R^2$ and $R^3$ are as hereinbefore defined and P represents a phenolic hydroxy protecting group). The choice of phenolic hydroxy protecting group P is within the standard knowledge of an organic chemist, for example those included in standard texts such as "Protective Groups in Organic Synthesis" T. W. Greene and R. G. M. Wuts, 2nd Ed. Wiley 1991, including ethers (for example, methyl, methoxymethyl, allyl and benzyl), silyl ethers (for example, t-butyldiphenylsilyl and t-butyldimethylsilyl), esters (for example, acetate and benzoate) and carbonates (for example, methyl and benzyl). The removal of such a phenolic hydroxy protecting group may be effected by any of the procedures known for such a transformation, including those reaction conditions indicated in standard texts such as that indicated hereinbefore, or by a related procedure. The reaction conditions preferably being such that the hydroxy derivative is produced without unwanted reactions at other sites within the starting or product compounds. For example, where the protecting group P is acetate, the transformation may conveniently be effected by treatment of the quinazoline derivative with a base as defined hereinbefore and including ammonia, and its mono and di-alkylated derivatives, preferably in the presence of a protic solvent or co-solvent such as water or an alcohol, for example methanol or ethanol. Such a reaction can be effected in the presence of an additional inert solvent or diluent as defined hereinbefore and at a temperature in the range 0 to 50° C., conveniently at about 20° C.

(c) Production of compounds of formula I and salts thereof can be achieved by the reaction, conveniently in the presence of a base as defined hereinbefore, of a compound of the formula VI:

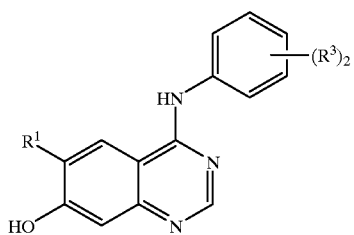

(VI)

(wherein $R^1$ and $R^3$ are as hereinbefore defined) with a compound of formula VII:

 (VII)

(wherein $L^1$ is as hereinbefore defined and $R^4$ is methyl, ethyl, 2-methoxyethyl, 3-methoxypropyl, 2-ethoxyethyl, trifluoromethyl, 2,2,2-trifluoroethyl, 2-hydroxyethyl, 3-hydroxypropyl, 2-(N,N-dimethylamino)ethyl, 3-(N,N-dimethylamino)propyl, 2-morpholinoethyl, 3-morpholinopropyl, 4-morpholinobutyl, 2-piperidinoethyl, 3-piperidinopropyl, 4-piperidinobutyl, 2-(piperazin-1-yl)ethyl, 3-(piperazin-1-yl)propyl, 4-(piperazin-1-yl)butyl, 2-(4-methylpiperazin-1-yl)ethyl, 3-(4-methylpiperazin-1-yl)propyl or 4-(4-methylpiperazin-1-yl)butyl); $L^1$ is a displaceable moiety for example a halogeno or sulphonyloxy group such as a bromo or methanesulphonyloxy group. The reaction is preferably effected in the presence of a base (as defined hereinbefore in process (a)) and advantageously in the presence of an inert solvent or diluent (as defined hereinbefore in process (a)), advantageously at a temperature in the range, for example 10 to 1 50° C., conveniently at about 50° C.

(d) Compounds of the formula I and salts thereof may be prepared by the reaction of a compound of the formula VIII:

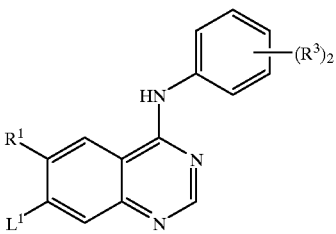

(VIII)

with a compound of the formula IX:

 (IX)

(wherein $L^1$, $R^1$, $R^2$ and $R^3$ are all as hereinbefore defined). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about (e) Compounds of the formula I and salts thereof wherein $R^2$ is $R^5C_{1-4}$alkoxy, in particular $R^5C_{1-3}$alkoxy, (wherein $R^5$ is selected from methoxy, ethoxy, hydroxy, N,N-dimethylamino, morpholino, piperidino, piperazin-1-yl or 4-methylpiperazin-1-yl) may be prepared by reacting a compound of the formula X:

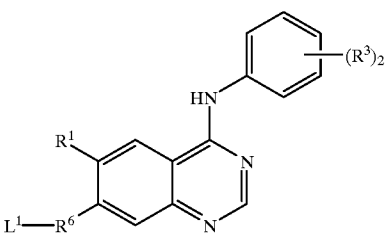

(X)

(wherein $L^1$, $R^1$ and $R^3$ are as hereinbefore defined and $R^6$ is $C_{1-4}$alkoxy, in particular $C_{1-3}$alkoxy) with a compound of the formula XI:

 (XI)

(wherein $R^5$ is as defined hereinbefore) to give a compound of the formula I. The reaction may conveniently be effected in the presence of a base (as defined hereinbefore in process (a)) and advantageously in the presence of an inert solvent or diluent (as defined hereinbefore in process (a)), and at a temperature in the range, for example 0 to 150° C., conveniently at about 50C.

Synthesis of Intermediates (i) Compounds of formula III and salts thereof constitute a further feature of the present invention. Such compounds in which $L^1$ is halogeno may for example be prepared by halogenating a compound of the formula XII:

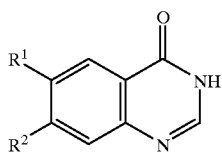

(XII)

(wherein $R^1$ and $R^2$ are as hereinbefore defined).

Convenient halogenating agents include inorganic acid halides, for example thionyl chloride, phosphorus(III) chloride, phosphorus(V)oxychloride and phosphorus(V) chloride. The halogenation reaction is conveniently effected in the presence of an inert solvent or diluent such as for example a halogenated solvent such as methylene chloride, trichloromethane or carbon tetrachloride, or an aromatic hydrocarbon solvent such as benzene or toluene. The reaction is conveniently effected at a temperature in the range, for example 10 to 150° C., preferably in the range 40 to 1 00° C.

The compounds of formula XII and salts thereof which constitute a further feature of the present invention may for example be prepared by reacting a compound of the formula XIII:

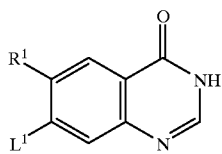

(XIII)

(wherein $R^1$ and $L^1$ are as hereinbefore defined) with a compound of the formula IX as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

The compounds of formula XII and salts thereof may also be prepared by cyclising a compound of the formula XIV:

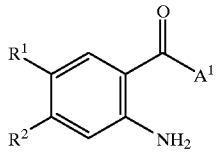

(XIV)

(wherein $R^1$ and $R^2$ are as hereinbefore defined, and $A^1$ is an hydroxy, alkoxy (preferably $C_{1-4}$alkoxy) or amino group) whereby to form a compound of formula XII or salt thereof. The cyclisation may be effected by reacting a compound of the formula XIV, where $A^1$ is an hydroxy or alkoxy group, with formamide or an equivalent thereof effective to cause cyclisation whereby a compound of formula XII or salt thereof is obtained, such as [3-(dimethylamino)-2-azaprop-2-enylidene]dimethylammonium chloride. The cyclisation is conveniently effected in the presence of formamide as solvent or in the presence of an inert solvent or diluent such as an ether for example 1,4-dioxan. The cyclisation is conveniently effected at an elevated temperature, preferably in the range 80 to 200° C. The compounds of formula XII may also be prepared by cyclising a compound of the formula XIV, where $A^1$ is an amino group, with formic acid or an equivalent thereof effective to cause cyclisation whereby a compound of formula XII or salt thereof is obtained. Equivalents of formic acid effective to cause cyclisation include for example a tri-$C_{1-4}$alkoxymethane, for example triethoxymethane and trimethoxymethane. The cyclisation is conveniently effected in the presence of a catalytic amount of an anhydrous acid, such as a sulphonic acid for example p-toluenesulphonic acid, and in the presence of an inert solvent or diluent such as for example a halogenated solvent such as methylene chloride, trichloromethane or carbon tetrachloride, an ether such as diethylether or tetrahydrofuran, or an aromatic hydrocarbon solvent such as toluene. The cyclisation is conveniently effected at a temperature in the range, for example 10 to 100° C, preferably in the range 20 to 50° C.

Compounds of formula XIV and salts thereof, which constitute a further feature of the present invention, may for example be prepared by the reduction of the nitro group in a compound of the formula XV:

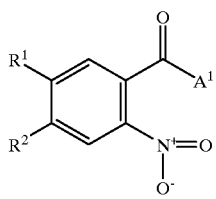

(XV)

(wherein $R^1$, $R^2$ and $A^1$ are as hereinbefore defined) to yield a compound of formula XIV as hereinbefore defined. The reduction of the nitro group may conveniently be effected by any of the procedures known for such a transformation. The reduction may be carried out, for example, by the hydrogenation of a solution of the nitro compound in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound and the activated metal in the presence of a solvent or diluent such as a mixture of water and alcohol, for example methanol or ethanol, to a temperature in the range, for example 50 to 150° C., conveniently at about 70° C.

Compounds of the formula XV and salts thereof which constitute a further feature of the present invention, may for example be prepared by the reaction of a compound of the formula XVI:

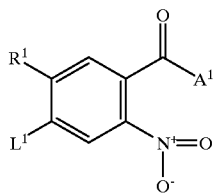

(XVI)

(wherein $R^1$, $L^1$ and $A^1$ are as hereinbefore defined) with a compound of the formula IX as hereinbefore defined to give a compound of the formula XV. The reaction of the compounds of formulae XVI and IX is conveniently effected under conditions as described for process (d) hereinbefore.

Compounds of formula XV and salts thereof, may for example also be prepared by the reaction of a compound of the formula XVII:

(XVII)

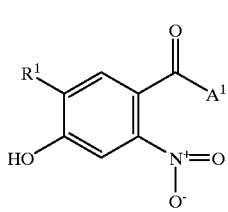

(wherein $R^1$ and $A^1$ are as hereinbefore defined) with a compound of the formula VII as hereinbefore defined to yield a compound of formula XV as hereinbefore defined. The reaction of the compounds of formulae XVII and VII is conveniently effected under conditions as described for process (c) hereinbefore.

The compounds of formula III and salts thereof may also be prepared for example by reacting a compound of the formula XVIII:

(XVIII)

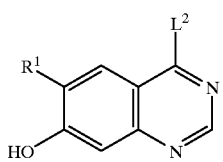

(wherein $R^1$ is as hereinbefore defined and $L^2$ represents a displaceable protecting moiety) with a compound of the formula VII as hereinbefore defined, whereby to obtain a compound of formula III in which $L^1$ is represented by $L^2$.

A compound of formula XVIII is conveniently used in which $L^2$ represents a phenoxy group which may if desired carry up to 5 substituents, preferably up to 2 substituents, selected from halogeno, nitro and cyano. The reaction may be conveniently effected under conditions as described for process (c) hereinbefore.

The compounds of formula XVIII and salts thereof as hereinbefore defined may for example be prepared by deprotecting a compound of the formula XIX:

(XIX)

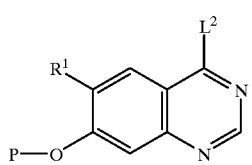

(wherein $R^1$, P and $L^2$ are as hereinbefore defined). Deprotection may be effected by techniques well known in the literature, for example where P represents a benzyl group deprotection may be effected by hydrogenolysis or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula XII as hereinbefore defined, followed by introduction of halide to the compound of formula XII, thus obtained as hereinbefore defined, to yield a compound of formula III in which $L^1$ represents halogen.

(ii) The compounds of formula V and salts thereof, constitute a further feature of the present invention, and may for example be prepared by the reaction of a compound of formula III as hereinbefore defined with a compound of the formula XX:

(XX)

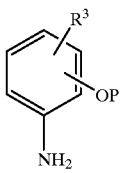

(wherein $R^3$ and P are as hereinbefore defined). The reaction may for example be effected as described for process (a) hereinbefore.

The compounds of formula V and salts thereof may also be prepared by reacting a compound of formula XXI:

(XXI)

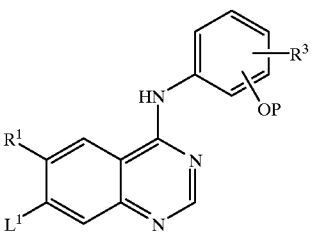

(wherein $R^1$, $L^1$, $R^3$ and P are as hereinbefore defined) with a compound of formula IX as hereinbefore defined. The reaction may for example be effected as described for process (d) above.

The compounds of formula V and salts thereof may also be prepared by reacting a compound of formula XXII:

(XXII)

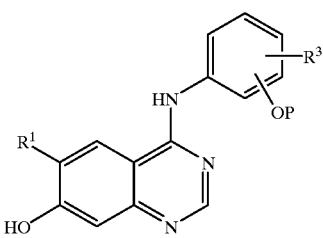

(wherein $R^1$, $R^3$ and P are as hereinbefore defined) with a compound of the formula VII as hereinbefore defined. The reaction may for example be effected as described for process (c) hereinbefore.

The compounds of formula XXI and salts thereof may for example be prepared by reaction of a compound of formula XXIII:

(XXIII)

(wherein $R^1$ and $L^1$ are as hereinbefore defined, and $L^1$ in the 4- and 7-positions may be the same or different) with a compound of the formula XX as hereinbefore defined. The reaction may be effected for example by a, process as described in (a) above.

Compounds of the formula XXII and salts thereof may be made by reacting compounds of the formulae XIX and XX as hereinbefore defined, under conditions described in (a) hereinbefore, to give a compound of formula XXIV:

(XXIV)

(wherein $R^1$, $R^1$ and P are as hereinbefore defined) and then deprotecting the compound of formula XXIV for example as described in (i) above.

(iii) Compounds of the formula VI as hereinbefore defined and salts thereof may be made by deprotecting the compound of formula XXV:

(XXV)

(wherein $R^1$, $R^3$ and P are as hereinbefore defined) by a process for example as described in (i) above.

Compounds of the formula XXV and salts thereof may be made by reacting compounds of the formulae XIX and IV as hereinbefore defined, under the conditions described in (a) hereinbefore, to give a compound of the formula XXV or salt thereof.

(iv) Compounds of the formula VIII and salts thereof as hereinbefore defined may be made by reacting compounds of the formulae XXIII and IV as hereinbefore defined, the reaction for example being effected by a process as described in (a) above.

(v) Compounds of the formula X as defined hereinbefore and salts thereof may for example be made by the reaction of a compound of formula VI as defined hereinbefore with a compound of formula XXVI:

$$L^1—R^6L—L^1 \quad (XXVI)$$

(wherein $L^1$ and $R^6$ are as hereinbefore defined) to give a compound of the formula X. The reaction may be effected for example by a process as described in (c) above.

Compounds of the formula X and salts thereof may also be made for example by deprotecting a compound of the formula XXVII:

(XXVII)

(wherein $L^1$, $R^6$, $R^1$, $R^3$ and P are as defined hereinbefore) by a process for example as described in (b) above.

Compounds of the formula XXVII and salts thereof may be made for example by reacting compounds of the formulae XXII and XXVI as defined hereinbefore, under the conditions described in (c) above.

When a pharmaceutically acceptable salt of a compound of the formula I is required, it may be obtained, for example, by reaction of said compound with, for example, an acid using a conventional procedure, the acid having a pharmaceutically acceptable anion.

Many of the intermediates defined herein are novel, for example, those of the formulae III, V, XII, XIV and XV, and these are provided as a further feature of the invention.

Intermediates of the formulae VI, VIII, X, XXI, XXII, XXIV, XXV and XXVII are also provided as a further feature of the invention.

The identification of compounds which potently inhibit the tyrosine kinase activity associated with the VEGF receptors such as Flt and/or KDR and which inhibit angiogenesis and/or increased vascular permeability is desirable and is the subject of the present invention. These properties may be assessed, for example, using one or more of the procedures set out below:

(a) In Vitro Receptor Tyrosine Kinase Inhibition Test

This assay determines the ability of a test compound to inhibit tyrosine kinase activity. DNA encoding VEGF or epidermal growth factor (EGF) receptor cytoplasmic domains may be obtained by total gene synthesis (Edwards M, International Biotechnology Lab 5(3), 19–25, 1987) or by cloning. These may then be expressed in a suitable expression system to obtain polypeptide with tyrosine kinase activity. For example VEGF and EGF receptor cytoplasmic domains, which were obtained by expression of recombinant protein in insect cells, were found to display intrinsic tyrosine kinase activity. In the case of the VEGF receptor Flt (Genbank accession number X51602), a 1.7 kb DNA fragment encoding most of the cytoplasmic domain, commencing with methionine 783 and including the termination codon, described by Shibuya et al (Oncogene, 1990, 5: 519–524), was isolated from cDNA and cloned into a baculovirus transplacement vector (for example pAcYM I (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example Spodoptera frugiperda 21 (Sf2 1)) with viral DNA (eg Pharningen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947) and methionine 668 (EGF receptor, Genbank accession number X00588) may be cloned and expressed in a similar manner.

For expression of cFlt tyrosine kinase activity, Sf12 cells were infected with plaque-pure cFlt recombinant viris at a multiplicity of infection of 3 and harvested 48 hours later. Harvested cells were washed with ice cold phosphate buffered saline solution (PBS) (10 mM sodium phosphate pH7.4, 138mM NaCl, 2.7 mM KCl) then resuspended in ice cold HNTG/PMSF (20 mM Hepes pH7.5, 150 mM NaCl, 10% v/v glycerol, 1% v/v Triton X100, 1.5 mM $MgCl_2$, 1 mM ethylene glycol-bis(paminoethyl ether) N,N,N',N'-tetraacetic acid (EGTA), 1 mM PMSF (phenylmethylsulphonyl fluoride); the PMSF is added just before use from a freshly-prepared 100 mA solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM $Na_3VO_4$, 0.1% v/v Triton X100, 0.2mM dithiothreitol). For a typical batch, stock enzyme is diluted 1 in 2000 with enzyme diluent and 50 μl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 μl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH7.4.

Test compounds were diluted with 10% dimethylsulphoxide (DMSO) and 25μl of diluted compound was transferred to wells in the washed assay plates. "Total" control wells contained 10% DMSO instead of compound. Twenty five microliters of 40 mM $MnCl_2$ containing 8 μM adenosine-5'-triphosphate (ATP) was added to all test wells except "blank" control wells which contained $MnCl_2$ without ATP. To start the reactions 50 μl of freshly diluted enzyme was added to each well and the plates were incubated at room temperature for 20 minutes. The liquid was then discarded and the wells were washed twice with PBST. One hundred microlitres of mouse IgG anti-phosphotyrosine antibody (Upstate Biotechnology Inc. product 05-321), diluted 1 in 6000 with PBST containing 0.5% w/v bovine serum albumin (BSA), was added to each well and the plates were incubated for I hour at room temperature before discarding the liquid and washing the wells twice with PBST. One hundred microliters of horse radish peroxidase(HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST. One hundred microliters of 2,2'-azino-bis(3-ethylbenzthiazoline-6suphonic acid) (ABTS) solution, freshly prepared using one 50 mg ABTS tablet (Boelcringer 1204 521) in 50 ml freshly prepared 50 mM phosphate-citrate buffer pH1.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibtion of enzyme activity.

(b) In Vitro HUVEC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL) +7.5% v/v foetal calf serum (FCS) and were plated out (at passage 2 to 8), in MCDB 131+2% v/v FCS+3 μg/ml heparin+1 μg/ml hydrocortisone, at a concentration of 1000 cell s/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% $CO_2$. On day 4 the cultures were pulsed with 1 μCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation, of radioactivity into cells, expressed as cpm, was used to measure inhibit ion of growth factor-stimulated cell proliferation by compounds.

(c) In Vivo Rat Uterine Oedema Assay

This test measures the capacity of compounds to reduce the acute increase in uterine weight in rats which occurs in the first 4–6 hours following oestrogen stimulation. This early increase in uterine weight has long been known to be due to oedema caused by increased peroeability of the uterine vasculature and recently Cullinan-Bove and Koos (Endocrinology, 1993,133:829–837) demonstrated a close temporal relationship with increased expression of VEGF mRNA in the uterus. We have found that prior treatment of the rats with a neutralising monoclonal antibody to VEGF significantly reduces the acute increase in uterine weight, confirming that the increase in weight is substantially mediated by VEGF.

Groups of 20 to 22-day old rats were treated with a single subcutaneous dose of oestradiol benzoate (2.5 μg/rat) in a solvent, or solvent only. The latter served as unstimulated controls. Test compounds were orally administered at various times prior to the administration of oestradiol benzoate. Five hours after the administration of oestradiol benzoate the rats were humanely sacrificed and their uteri were dissected, blotted and weighed. The increase in uterine weight in groups treated with test compound and oestradiol benzoate and with oestradiol benzoate alone was compared using a Student T test. Inhibition of the effect of oestradiol benzoate was considered significant when p<0.05.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square meter body area of the animal., i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and are therefore of interest for their antiangiogenic effects and/or their ability to cause a reduction in vascular permeability.

A further feature of the present invention is a compound of formula I, or a pharmaceutically acceptable salt thereof, for use as a medicament, conveniently a compound of formula I, or a pharmaceutically acceptable salt thereof, for use as a medicament for producing an antiangiogenic and/or vascular permeability reducing effect in a warm-blooded animal such as a human being.

Thus according to a further aspect of the invention there is provided the use of a compound of the formula 1, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varied depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:

(i) other antiangiogenic agents that work by different mechanisms from those defined hereinbefore (for example linomide, inhibitors of integrin avβ3 function, angiostatin, razoxin, thalidomide);

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincrisitine and taxoids like taxol, taxotere); topoisomerase inhibitors (for example epipodophyllotoxins like etoposide and teniposide, amsacrine, topotecan).

As stated above the compounds defined in the present invention are of interest for their antiangiogenic and/or vascular permeability reducing effects. Such compounds of the invention may therefore be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation and ocular diseases with retinal vessel proliferation. In particular such compounds of the invention are expected to slow advantageously the growth of primary and recurrent solid turnours of, for example, the colon, breast, prostate, lungs and skin. More particularly such compounds of the invention are expected to inhibit the growth of those primary and recurrent solid tumours which are associated with VEGF, especially those tumours which are significantly dependent on VEGF for their growth and spread, including for example, certain tumours of the colon, breast, prostate, lung, vulva and skin.

Furthermore compounds of the present invention may be particularly useful in any of the disease states listed above such as cancer in which VEGF is a significant contributing factor to angiogenesis and in which EGF is contributing less than VEGF to angiogenesis.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:

[(i) evaporations were carried out by rotary evaporation in vacuo and work-up procedures were carried out after removal of residual solids such as drying agents by filtration;

(ii) operations were carried out at ambient temperature, that is in the range 18–25° C. and under an atmosphere of an inert gas such as argon;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany;

(iv) yields are given for illustration only and are not necessarily the maximum attainable;

(v) melting points are uncorrected and were determined using a Mettler SP62 automatic melting point apparatus, an oil-bath apparatus or a Koffler hot plate apparatus.

(vi) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, broad; q, quartet;

(vii) intermediates were not generally fully characterised and purity was assessed by thin layer chromatography (TLC), high-performance liquid chromatography (HPLC), infra-red (IR) or NMR analysis;

(viii) the following abbreviations have been used:
DMF N,N-dimethylformamide
DMSO dimethylsulphoxide
THF tetrahydrofuran
NMP 1-methyl-2-pyrrolidinone
TFA trifluoroacetic acid.]

EXAMPLE 1

A solution of 4-chloro-7-(2-methoxyethoxy)quinazoline hydrochloride (624 mg, 2.27 mmol) and 4-chloro-2-fluoroaniline (305 μl, 2.6 mmol) in isopropanol (20 ml) was heated at reflux for 30 minutes. The solvent was removed by evaporation and the residue partitioned between ethyl acetate and water. The organic layer was separated, washed with aqueous sodium hydrogen carbonate solution, then with water, dried ($MgSO_4$) and the solvent removed by evaporation. The residue was triturated with ether to give 4-(4-chloro-2-fluoroanilino)-7-(2-methoxyethoxy) quinazoline (662 mg, 84%) as a white solid.

m.p 140–141° C.

$^1$H NMR Spectrum: ($DMSOd_6$) 3.35(s, 3H); 3.74(t, 2H); 4.29(t, 2H); 7.21(s, 1H); 7.28(d, 1H); 7.35(d, 1H); 7.6(m, 2H); 8.36(d, 1H); 8.43(s, 1H); 9.75(s, 1H)

MS-ESI: 347 [MH]$^+$

| Elemental analysis: | Found | C 58.49 | H 4.41 | N 12.08 |
|---|---|---|---|---|
| $C_{17}H_{15}N_3O_2FCl$ | Requires | C 58.70 | H 4.31 | N 12.08% |

The starting material was prepared as follows:

A solution of 2-amino-4-fluorobenzoic acid (3 g, 19.3 mmol) in formamide (30 ml) was heated at 150° C. for 6 hours. The reaction mixture was poured onto ice/water (1/1) (250 ml). The precipitated solid was collected by filtration, washed with water and dried to give 7-fluoro-3,4-dihydroquinazolin-4-one (2.6 g, 82%).

Sodium (400 mg, 17 mmol) was added carefully to 2-methoxyethanol (10 ml) and the mixture heated at reflux for 30 minutes. 7-Fluoro-3,4-dihydroquinazolin-4-one (750 mg, 4.57 mmol) was added to the resulting solution and the mixture heated at reflux for 15 hours. The mixture was cooled and poured into water (250 ml). The mixture was acidified to pH4 with concentrated hydrochloric acid. The resulting solid product was collected by filtration, washed with water and then with ether, and dried under vacuum to give 7-(2-methoxyethoxy)-3,4-dihydroquinazolin4-one (580 mg, 58%).

A solution of 7-(2-methoxyethoxy)-3,4-dihydroquinazolin-4-one (500 mg, 2.2 mmol) in thionyl chloride (15 ml) and DMF (0.1 ml) was heated at reflux for 3 hours. The volatiles were removed by evaporation to give 4-chloro-7-(2-methoxyethoxy)quinazoline hydrochloride as a cream solid (520 mg, 83%).

EXAMPLE 2

4-Chloro-6,7-dimethoxyquinazoline hydrochloride (342 mg, 1.3 mmol), and 2-fluoro-5-hydroxyaniline (183 mg, 1.4 mmol) in isopropanol (10 ml) were heated at reflux for 2 hours. The reaction mixture was allowed to cool, the precipitated product collected by filtration, washed with isopropanol and dried to give 6,7-dimethoxy4-(2-fluoro-5-hydroxyanilino)quinazoline hydrochloride (66 mg, 15%) as a solid.

m.p. 219–220° C.

$^1$H NMR Spectrum: ($DMSOd_6$) 3.99(s, 3H); 4.01(s, 3H); 6.81(dd, 1H); 6.90(dd, 1H); 7.20(t, 1H); 7.31(s, 1H); 8.15(s, 1H); 8.81(s, 1H); 9.72(s, 1H); 11.28(s, 1H)

MS-ESI: 316 [MH]$^+$

| Elemental analysis: | Found | C 53.5 | H 5.3 | N 9.9 |
|---|---|---|---|---|
| $C_{16}H_{14}N_3O_3F$ HCl 0.5$H_2O$ 0.5$C_3H_8O$ | Requires | C 53.8 | H 5.1 | N 10.7% |

The starting material was prepared as follows:

A mixture of 4,5-dimethoxyanthranilic acid (19.7 g) and formamide (10 ml) was stirred and heated at 190° C. for 5 hours. The mixture was allowed to cool to approximately 80° C. and water (50 ml) was added. The mixture was stored at ambient temperature for 3 hours. The precipitate was isolated, washed with water and dried to give 6,7-dimethoxy-3,4-dihydroquinazolin-4one (3.65 g).

A mixture of a portion (2.06 g) of the material so obtained, thionyl chloride (20 ml) and DMF (1 drop) was stirred and heated at reflux for 2 hours. The volatiles were removed by evaporation to give 4-chloro-6,7-dimethoxyquinazoline hydrochloride.

4-Chloro-5-methoxycarbonyloxy-2-fluoronitrobenzene (1.2 g, 4.8 mmol), (as described in EP 61741 A2), and 10% palladium-on-charcoal catalyst (500 mg) in ethanol (100 ml) was stirred under hydrogen at 1 atmosphere pressure for 18 hours. A further batch of 10% palladium-on-charcoal catalyst (500 mg) was added and the mixture stirred under hydrogen for a further 3 hours. The catalyst was removed by filtration through diatomaceous earth and the solvent removed from the filtrate by evaporation. The residue was purified by flash chromatography eluting with methylene chloride/hexane (1/4) to give 2-fluoro-5-methoxycarbonyloxyaniline (0.42 g, 47%) as an oil.

$^1$H NMR Spectrum: (DMSOd$_6$) 3.82(s, 3H); 5.33(s, 2H); 6.32(dt, 1H); 6.57(dd, 1H); 6.98(dd, 1H)

MS-ESI: 186 [MH]$^+$

Concentrated aqueous ammonia (15 ml) was added to a solution of 2-fluoro-5-methoxycarbonyloxyaniline (400 mg, 2.16 mmol) in methanol (10 ml). The mixture was stirred for 2 hours and most of the solvent was removed by evaporation. The resulting suspension was diluted with water, acidified to pH7 and extracted with ethyl acetate. The organic extracts were washed with water, dried (MgSO$_4$) and solvent removed by evaporation to give 2-fluoro-5-hydroxyaniline (200 mg, 73%).

$^1$H NMR Spectrum: (DMSOd$_6$) 4.90(s, 2H); 5.84(dd, 1H); 6.17(dd, 1H); 6.65(ddd, 1H); 8.80(s, 1H)

EXAMPLE 3

A mixture of 4-chloro-6,7-dimethoxyquinazoline hydrochloride (500 mg, 1.916 mmol), (prepared as described for the starting material in Example 2), and 4-chloro-3-hydroxyaniline (300 mg, 2.09 mmol), (as described in UK patent 1427658), in isopropanol (10 ml) was heated at reflux for 2 hours. The mixture was allowed to cool, the solid product collected by filtration, washed with isopropanol and dried to give 4-(4-chloro-3-hydroxyanilino)-6,7-dimethoxyquinazoline hydrochloride (605 mg, 86%). m.p. >250° C.

$^1$H NMR Spectrum: (DMSOd$_6$) 4.02(s, 3H); 4.04(s, 3H); 7.15(dd, 1H); 7.34–7.44(m, 3H); 8.28(s, 1H); 8.82(s, 1H); 10.52(s, 1H); 11.24(s, 1H)

MS: 332 [MH]$^+$

| Elemental analysis: | Found | C 52.4 | H 4.2 | N 11.3 |
|---|---|---|---|---|
| C$_{16}$H$_{14}$N$_3$O$_3$Cl 1HCl | Requires | C 52.2 | H 4.1 | N 11.4% |

EXAMPLE 4

2-Bromoethyl methyl ether (712 µl, 7.56 mmol) was added dropwise to a solution of 4-(4-chloro-2-fluoroanilino)-7-hydroxy-6-methoxyquinazoline (2.2 g, 6.88 mmol) and potassium carbonate (2.84 g, 20.6 mmol) in DMF (110 ml). The mixture was stirred for 10 hours at 60° C. then for 2 days at ambient temperature, the solvent was removed by evaporation and the crude product purified by flash chromatography eluting with ethyl acetate/petroleum ether (4/1). The resulting solid was dissolved in hot ethanol and ethanolic hydrogen chloride was added. After cooling, the resulting solid was collected by filtration, washed with ethanol and dried under vacuum to give 4-(4-chloro-2-fluoroanilino)-6-methoxy-7-(2-methoxyethoxy)quinazoline hydrochloride (1.74 g, 62%).

m.p. 255–257° C.

$^1$H NMR Spectrum: (DMSOd$_6$; CD$_3$COOD) 3.36(s, 3H); 3.79(t, 2H); 4.02(s, 3H); 4.34(t, 2H); 7.33(s, 1H); 7.46(dd, 1H); 7.60–7.68(m, 2H); 8.15(s, 1H); 8.79(s, 1H)

| Elemental analysis: | Found | C 52.1 | H 4.6 | N 10.1 |
|---|---|---|---|---|
| C$_{18}$H$_{17}$N$_3$O$_3$ClF 1HCl | Requires | C 52.19 | H 4.38 | N 10.14% |

The starting material was prepared as follows:

A mixture of 2-amino-4-benzyloxy-5-methoxybenzamide (J. Med. Chem. 1977, vol 20, 146–149, 10 g, 0.04 mol) and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The volatiles were removed by evaporation, water was added to the residue, the solid was collected by filtration, washed with water and dried. Recrystallisation from acetic acid gave 7-benzyloxy-6-methoxy-3,4-dihydroquinazolin-4-one (8.7 g, 84%).

A mixture of 7-benzyloxy-6-methoxy-3,4-dihydroquinazolin-4-one (2.82 g, 0.01 mol), thionyl chloride (40 ml) and DMF (0.28 ml) was stirred and heated at reflux for 1 hour. The volatiles were removed by evaporation, the residue was azeotroped with toluene to give 7-benzyloxy-4-chloro-6-methoxyquinazoline hydrochloride (3.45 g).

A solution of 7-benzyloxy-4-chloro-6-methoxyquinazoline hydrochloride (1.2 g, 3.5 mmol) and 4-chloro-2-fluoroaniline (444 µl, 4 mmol) in isopropanol (40 ml) was refluxed for 1.5 hours. After cooling, the precipitate was collected by filtration, washed with isopropanol then ether and dried under vacuum to give 7-benzyloxy-4-(4-chloro-2-fluoroanilino)-6-methoxyquinazoline hydrochloride (1.13 g, 71%).

m.p. 239–242° C.

$^1$H NMR Spectrum: (DMSOd$_6$) 4.0(s, 3H); 5.36(s, 2H); 7.39–7.52(m, 9H); 8.1(s, 1H); 8.75(s, 1H)

MS-ESI: 410 [MH]$^+$

| Elemental analysis: | Found | C 59.2 | H 4.3 | N 9.4 |
|---|---|---|---|---|
| C$_{22}$H$_{17}$N$_3$O$_2$ClF 1HCl | Requires | C 59.21 | H 4.07 | N 9.41% |

A solution of 7-benzyloxy-4-(4-chloro-2-fluoroanilino)-6-methoxyquinazoline hydrochloride (892 mg, 2 mmol) in TFA (10 ml) was refluxed for 50 minutes. After cooling, the mixture was poured onto ice. The precipitate was collected by filtration, dissolved in methanol (10 ml) and basified to pH11 with aqueous ammonia. After concentration by evaporation, the solid product was collected by filtration, washed with water then ether and dried under vacuum to give 4-(4-chloro-2-fluoroanilino)-7-hydroxy-6-methoxyquinazoline as a yellow solid (460 mg, 72%).

m.p. 141–143° C.

$^1$H NMR Spectrum: (DMSOd$_6$) 3.95(s, 3H); 7.05(s, 1H); 7.35(d, 1H); 7.54–7.59(m, 2H); 7.78(s, 1I); 8.29(s, 1H)

MS-ESI: 320–322 [MH]$^+$

EXAMPLE 5

A mixture of 4-chloro-6,7-dimethoxyquinazoline hydrochloride (147 mg, 0.56 mmol), (prepared as described for the starting material in Example 2), and 4-chloro-2-fluoroaniline (82 mg, 0.56 mmol) in isopropanol (7 ml) was heated at reflux for 2 hours. The mixture was allowed to cool, the solid product collected by filtration, washed with isopropanol and dried to give 4-(4-chloro-2-fluoroanilino)-6,7-dimethoxyquinazoline hydrochloride (102 mg, 49%).

$^1$H NMR Spectrum: (DMSOd$_6$) 4.00(s, 6H); 7.37(s, 1H); 7.42(d, 1H); 7.60(t, 1H); 7.67(dd, 1H); 8.27(s, 1H); 8.80 (s, 1H)

MS-ESI: 334 [MH]$^+$

EXAMPLE 6

4-(3-Chloropropyl)morpholine (J. Am. Chem. Soc. 1945, 67, 736, 174 mg, 1.06 mmol) in DMF (0.5 ml) was added to a stirred suspension of 4-(3-t-butyldiphenylsilyloxy-4-methylanilino)-7-hydroxy-6-niethoxyquinazoline (471 mg, 0.88 mmol) and potassium carbonate (200 mg, 1.45 mmol) in DMF (5 ml). The mixture was then heated at 100° C. for 2.5 hours. The solvent was removed by evaporation, and the residues partitioned between methylene chloride and water. The product was extracted with methylene chloride and the combined extracts passed through phase separating paper. The solvent was removed by evaporation to give a yellow oil. This oil was dissolved in THF (4 ml and tetra-n-butylammonium fluoride (2 ml of a 1M solution in THF, 2 mmol) added. The mixture was stirred at ambient temperature for 72 hours, the solvent was removed by evaporation and the residue partitioned between methylene chloride and saturated aqueous sodium hydrogen carbonate solution. The aqueous phase was extracted with methylene chloride (3×20 ml), the combined extracts passed through phase separating paper and the solvent removed by evaporation. The residue was purified by flash chromatography eluting with methanol/methylene chloride (1/9) to give 4-(3-hydroxy4-methylanilino)-6-methoxy-7-(3-morpholinopropoxy) quinazoline as a pale yellow solid (225 mg, 60% over two steps).

$^1$H NMR Spectrum: (DMSOd$_6$) 2.0(m, 2H); 2.15(s, 3H); 2.4(m, 4H); 3.6(t, 4H); 3.95(s, 3H); 4.20(t, 2H); 7.05(s, 2H); 7.15(s, 1H); 7.35(s, 1H); 7.85(s, 1H); 8.40(s, 1H); 9.25(s, 2H)

MS-ESI: 425 [MH]$^+$

The starting material was prepared as follows:

A mixture of 7-benzyloxy-6-methoxy-3,4-dihydroquinazolin-4-one (5.18 g, 18.4 mmol), (prepared as described for the starting material in Example 4), DMF (1 ml) and thionyl chloride (70 ml) was heated at reflux under argon for 2 hours. The mixture was allowed to cool, excess thionyl chloride was removed by evaporation and the residue azeotroped to dryness with toluene. The resulting crude 7-benzyloxy-4-chloro-6-methoxyquinazoline hydrochloride was suspended in isopropanol (50 ml) and 3-hydroxy4-methylaniline (2.60 g, 21.1 mmol) added. The mixture was heated at reflux for 3 hours and then allowed to cool. The precipitated product was collected by filtration, washed with isopropanol and dried to give 7-benzyloxy-4-(3-hydroxy-4-methylanilino)-6-methoxyquinazoline (4.7 g, 60%).

$^1$H NMR Spectrum: (DMSOd$_6$) 2.15 (s, 3H); 4.0(s, 3H); 5.35(s, 2H); 6.95(dd, 1H); 7.15(m, 2H); 7.35–7.55(m, 5H); 8.25(s, 1H); 8.75(s, 1H); 9.6(s, 1H); 11.2(s, 1H)

Imidazole (1.45 g, 21.6 mmol) was added to 7-benzyloxy-4-(3-hydroxy-4-methylanilino)-6-methoxyquinazoline (4.11 g, 9.69 mmol) in DMF (50 ml) and the mixture was stirred at ambient temperature until complete dissolution was achieved. t-Butyldiphenylsilyl chloride (2.5 ml, 9.6 mmol) was added dropwise and the reaction mixture stirred at ambient temperature for 72 hours. Saturated aqueous sodium hydrogen carbonate solution was added, and the product was extracted with methylene chloride. The solvent was removed by evaporation to give a damp solid which was dissolved in a mixture of DMF (40 ml), methanol (40 ml), and ethyl acetate (40 ml). 10% Palladium-on-charcoal catalyst (500 mg) was added and the mixture stirred under hydrogen at 1 atmosphere pressure for 36 hours. The catalyst was removed by filtration through diatomaceous earth, and the solvent removed from the filtrate by evaporation. The crude product was purified by flash chromatography eluting with methanol/methylene chloride (1/9) to give 4-(3-t-butyldiphenylsilyloxy-4-methylanilino)-7-hydroxy-6-methoxyquinazoline (2.2 g, 42% over two steps) as a yellow solid.

$^1$H NMR Spectrum : (DMSOd$_6$) 1.1 (s, 9H); 2.35(s, 3H); 3.90(s, 31H); 6.9(m, 2H); 7.1(d, 1H); 7.4(m, 6H); 7.5(d, 1H); 7.7(m, 51H); 7.85(s, 1H); 9.05(s, 1H); 10.2(s, 1H)

MS-ESI: 536 [MH]$^+$

EXAMPLE 7

A mixture of 7-(3-benzyloxypropoxy)-4-(4-chloro-2-fluoroanilino)-6-methoxyquinazoline hydrochloride (180 mg, 0.4 mmol) and 5% palladium-on-charcoal catalyst (50 mg) in methanol (5 m), trichloromethane (5 ml) a nd DMF (1 ml) was stirred under hydrogen at 1 atmosphere pressure for 2 hours. The catalyst was removed by filtration through diatomaceous earth and the solvent removed by evaporation. The residue was partitioned between ethyl acetate and aqueous sodium hydrogen carbonate solution, the organic layer separated and dried (MgSO$_4$) and the solvent removed by evaporation. The residue was recrystallised from ethyl acetate/hexane to give 4-(4-chloro-2-fluoroanilino)-7-(3-hydroxypropoxy)-6-methoxyquinazoline (48 mg, 33%).

m.p. 199–201° C.

$^1$H NMR Spectrum: (DMSOd$_6$) 1.92(t, 2H); 3.60(t, 2H); 3.95(s, 3H); 4.20(t, 2H); 4.55(t, 1H); 7.18(s, 1H); 7.33(dd, 1H); 7.51(dd, 1H); 7.55(td, 1H); 7.78(s, 1H): 8.38(s, 1H); 8.32(s, 1H); 9.50(s, 1H)

MS-ESI: 378 [MH]$^+$

| Elemental analysis: | Found | C 57.2 | H 4.6 | N 11.0 |
| $C_{18}H_{17}N_3O_3FCl$ | Requires | C 57.2 | H 4.5 | N 11.1% |

The starting material was prepared as follows:

A solution of 3-benzyloxy-1-propanol (150 μl, 0.9 mmol) was added to tributyephosphine (376 mg, 1.9 mmol) and 4-(4-chloro-2-fluoroanilino)-7-hydroxy-6-methoxyquinazoline (200 mg, 0.63 mmol), (prepared as described for the starting material in Example 4), in methylene chloride (20 ml) at 5° C. To the resulting mixture 1,1'-azodicarbonyldipiperidine (480 mg, 1.9 mmol) was added, the mixture stirred at 5° C. for 1 hour, allowed to warm to ambient temperature and stirred overnight. Ether (10 ml) was added, the mixture stirred for 15 minutes and the precipitated solids removed by filtration. The volatiles were removed from the filtrate by evaporation, and the residue was partitioned between ethyl acetate and water. The organic layer was separated, dried (MgSO$_4$) and the solvent removed by evaporation. The residue was dissolved in acetone, and hydrogen chloride in ether (0.6 ml of a 1M solution, 0.6 mmol) added. The resulting precipitated prod uct was collected by filtration and dried to give 7-(3-benzyloxypropoxy)4-(4-chloro-2-fluoroanilino)-6-methoxyquinazoline hydrochloride (90 mg, 31%).

$^1$H NMR Spectrum: (DMSOd$_6$) 2.22(t, 2H); 3.74(t, 2H); 4.10(s, 3H); 4.37(t, 2H); 4.60(s, 2H); 7.34–7.56(m, 7H); 7.68(t, 1H); 7.76(dd, 1H); 8.38(s, 1H); 8.90(s, 1H); 11.73(s, 1H)

EXAMPLE 8

4-($^2$-Chloroethyl)morpholine hydrochloride (40 mg, 2.1 mmol) was added to 4-(4-chloro-2-fluoroanilino)-7-hydroxy-6-methoxyquinazoline (63 mg, 0.2 mmol), (prepared as described for the starting material in Example 4), and potassium carbonate (95 mg, 0.69 mmol) in DMF (3 ml) and the mixture heated at 100° C. for 3 hours. The mixture was allowed to cool, the volatiles were removed by evaporation and the residues partitioned between water and methylene chloride. The organic phase was separated, passed through phase separating paper and the solvent was removed by evaporation. The residue was dissolved in acetone, and hydrogen chloride in ether (0.2 ml of a 1M solution, 0.2 mmol) was added. The precipitated product was collected by filtration and dried to give 4-(4-chloro-2-fluoroanilino)4-methoxy-7-(2-morpholinoethoxy)quinazoline hydrochloride (50 mg, 50%).

$^1$H NMR Spectrum: (DMSOd$_6$) 3.6(m, 2H); 3.85(m, 4H); 3.95(s, 3H); 4.6(m, 2H); 7.35(m, 2H); 7.6(m, 2H); 8.05(s, 1H); 8.55(s, 1H)

MS-ESI: 433 [MH]$^+$

| Elemental analysis: | Found | C 50.5 | H 4.9 | N 10.9 |
|---|---|---|---|---|
| $C_{21}H_{22}N_4O_3FCl$ 2HCl | Requires | C 49.9 | H 4.8 | N 11.1% |

EXAMPLE 9

4-(3-Chloropropyl)morpholine (J. Am. Chem. Soc. 1945, 67, 736, 2.26 g, 13.8 mmol) was added to 4-(4-chloro-2-fluoroanilino)-7-hydroxy-6-methoxyquinazoline (2.21 g, 6.9 mmol), (prepared as described for the starting material in Example 4). and potassium carbonate (6.5 g, 47 mmol) in DMF (100 ml). The mixture was heated at 110° C. for 4 hours and then allowed to cool. The volatiles were removed by evaporation and the residue was partitioned between water and methylene chloride. The organic phase was separated, washed with brine, passed through phase separating paper and the solvent removed by evaporation. The residue was purified by column chromatography eluting with methylene chloride/methanol/ammonia (aq.) (100/8/1). The product was dissolved in acetone and isopropanol and hydrogen chloride in ether (4.8 ml of a 1M solution, 4.8 mmol) was added. The precipitated product was collected by filtration and washed with acetone and ether to give 4-(4-chloro-2-fuoroanilino)-6-methoxy-7-(3-morpholinopropoxy)quinazoline hydrochloride (2.16 g, 65%).

$^1$H NMR Spectrum: (DMSOd$_6$) 2.25(m, 2H); 3.7–3.9(br s, 4H); 3.95(s, 3H); 4.25 (t, 2H); 7.2(s, 1H); 7.3(dt, 1H); 7.55(m, 2H); 7.95(s, 1H); 8.40(s, 1H); 9.85(br s, 1H);11.0(br s, 1H)

MS-ESI: 447 [MH]$^+$

| Elemental analysis: | Found | C 54.7 | H 5.6 | N 10.8 |
|---|---|---|---|---|
| $C_{22}H_{24}N_4O_3FCl$ 1HCl 0.5$C_3H_6O$ | Requires | C 55.1 | H 5.5 | N 10.9% |

EXAMPLE 10

Concentrated aqueous ammonia (8 ml) was added to a solution of 4-(3-acetoxy-4-methylanilino)-6-methoxy-7-(2-methoxyethoxy)quinazoline (2.38 g, 6 mmol) in a mixture of trichloromethane (24 ml) and methanol (24 ml). The mixture was heated at reflux for 8 hours and the volatiles removed by evaporation. The residue was triturated with water, the resulting solid was collected by filtration and recrystallised from methylene chloride/ethanol. The product was redissolved in a mixture of methylene chloride/ethanol and a saturated solution of hydrogen chloride in ethanol was added. The solvent was partially removed by evaporation and the mixture cooled. The resulting precipitate was collected by filtration washed with ether and dried under vacuum to give 4-(3-hydroxy-4-methylanilino)-6-methoxy-7-(2-methoxyethoxy)quinazoline hydrochloride (1.68 g, 80%).

m.p. 270° C. (decomposition)

$^1$H NMR Spectrum: (DMSOd$_6$; CF$_3$COOD) 2.17(s, 3H); 3.35(s, 3H); 3.78(t. 2H); 4.00(s, 3H); 4.33(t, 2H); 6.96(d, 1H); 7.08(s, 1H); 7.16(d, 1H); 7.3(s, 1H); 8.09(s, 1H): 8.81(s, 1H)

MS-ESI: 378 [MNa]$^+$

| Elemental analysis: | Found | C 58.0 | H 5.9 | 10.7 |
|---|---|---|---|---|
| $C_{19}H_{21}N_3O_4$1HCl | Requires | C 58.2 | H 5.7 | N 10.7% |

The starting material was prepared as follows:

Acetic anhydride (1.9 ml, 20.3 mmol) was added to a mixture of 2-methyl-5-nitrophenol (2.5 g, 1 6.3 mmol) and 1 M aqueous sodium hydroxide (24.5 ml) at ambient temperature. The mixture was stirred for 40 minutes, the solid was removed by filtration and the filtrate extracted with ethyl acetate. The combined organic extracts were washed with brine, dried (MgSO$_4$) and the solvent removed by evaporation to give 2-acetoxy4-nitrotoluene (3.1 g, 100%). A mixture of this material (3.1 g, 15.9 mmol) and 10% palladium-on-charcoal catalyst (0.12 g) in ethyl acetate (50 ml) was stirred at ambient temperature under hydrogen at 1 atmosphere pressure for 2 hours. The catalyst was removed by filtration through diatomaceous earth and the solvent removed from filtrate by evaporation to give 3-acetoxy-4-methylaniline (2.45 g, 94%).

A mixture of 7-benzyloxy4-chloro-6-methoxyquinazoline (2.18 g, 7.25 mmol), (prepared as described for the starting material in Example 4), 3-acetoxy-4-methylaniline (1.32 g, 8 mmol) and isopropanol (50 ml) was stirred and heated at reflux for 1 hour. The mixture was cooled to ambient temperature. The precipitate was collected by filtration, washed with isopropanol and ether to give 4-(3-acetoxy-4-methylanilino)-7-benzyloxy-6-methoxyquinazoline.

A mixture of 4-(3-acetoxy-4-methylanilino)-7-benzyloxy-6-methoxyquinazoline (2.68 g, 5.75 mmol) and 10% palladium-on-charcoal catalyst (0.27 g) in methanol (50 ml), DMF (12 ml) and trichloromethane (50 ml) was stirred at ambient temperature under hydrogen at 1.5 atmospheres pressure for 30 minutes. The catalyst was removed by filtration through diatomaceous earth and the solvent removed from filtrate by evaporation. The residue was triturated with ether, collected by filtration and dried under vacuum at 50° C. to give 4-(3-acetoxy-4-methylanilino)-7-hydroxy-6-methoxyquinazoline (2.1 g, 100%).

Potassium carbonate (2.2 g, 16 mmol) was added to a solution of 4-(3-acetoxy-4-methylanilino)-7-hydroxy-6-methoxyquinazoline (1.51 g, 4 mmol) in DMF (30 ml) and the mixture stirred for 15 minutes. 2-Bromoethyl methyl ether (667 mg, 4.8 mmol) was then added dropwise. The mixture was stirred for 1 hour at ambient temperature, then heated at 60° C. for 17 hours and finally allowed to cool. The insoluble material was removed by filtration and the filter pad washed with DMF. The filtrate was partitioned between ethyl acetate and water, the organic layer was separated, washed with brine, dried ($MgSO_4$) and the solvent removed by evaporation. The residue was purified by column chromatography eluting with methylene chloride/methanol (95/5 followed by 93/7). The purified product was triturated with ether to give 4-(3-acetoxy-4-methylanilino)-6-methoxy-7-(2-methoxyethoxy)quinazoline (1.34 g, 84%) as a white powder.

m.p. 180–183° C.

$^1$H NMR Spectrum: ($CDCl_3$) 2.16(s, 3H); 2.34(s, 3H); 3.47(s, 3H); 3.87(t, 2H); 3.99(s, 3H); 4.31(t, 2H); 6.98(s, 1H); 7.21(d, 1H); 7.24(d, 1H); 7.42(d, 1H); 7.50(s, 1H); .8.64(s, 1H)

MS-ESI: 420 [MNa]$^+$

| Elemental analysis: | Found | C 63.1 | H 6.1 | N 10.4 |
|---|---|---|---|---|
| $C_{21}H_{23}N_3O_5$ | Requires | C 63.5 | H 5.8 | N 10.6% |

EXAMPLE 11

A mixture of 4-chloro-6,7-dimethoxyquinazoline hydrochloride (130 mg, 0.5 mmol), (prepared as described for the starting material in Example 2), and 4-bromo-2-fluoroaniline (95 mg, 0.5 mmol) in isopropanol (7 ml) was heated at reflux for 2 hours. The mixture was allowed to cool to ambient temperature, the precipitated solid was collected by filtration, washed with isopropanol and ether and dried to give 4-(4-bromo-2-fluoroanilino)-6,7-dimethoxyquinazoline hydrochloride (124 mg, 60%) as an off-white solid. HPLC characteristics:

Column: 200×4.6 mm C18 ODS Hypersil (trade mark of Shandon) reversed phase 5 μm

Solvent: flow 1.5 ml/min.

0–3 minutes: $H_2O$/$CH_3CN$ (95/5) 0.03M triethylamine

3–17 minutes: gradient $H_2O$/$CH_3CN$ (95/5 to 5/95); constant 0.03M triethylamine Retention time: 13.01 minutes

EXAMPLE 12

A mixture of 4-chloro-6,7-dimethoxyquinazoline hydrochloride (130 mg, 0.5 mmol), (prepared as described for the starting material in Example 2), and 2-fluoro-4-methylaniline (63 mg, 0.5 mmol) in isopropanol (7 ml) was heated at reflux for 2 hours. The mixture was allowed to cool to ambient temperature, the precipitated solid was collected by filtration, washed with isopropanol and ether and dried to give 4-(2-fluoro-4-methylanilino)-6,7-dimethoxyquinazoline hydrochloride (87 mg, 50%) as an off-white solid.

HPLC Characteristics:

Column—200×4.6 mm $C_{18}$ ODS Hypersil (trade mark of Shandon) reversed phase 5μm Solvent—flow 1.5 ml/min.

0–3 minutes: $H_2O$/$CH_3CN$ (95/5) 0.03M triethylamine

3–17 minutes: gradient $H_2O$/$CH_3CN$ (95/5 to 5/95); constant 0.03M triethylamine Retention time—12.32 minutes

EXAMPLE 13

A mixture of 4-chloro-6,7-dimethoxyquinazoline hydrochloride (130 mg, 0.5 mmol), (prepared as described for the starting material in Example 2), and 3-hydroxy-4-methylaniline (62 mg, 0.5 mmol) in isopropanol (7 ml) was heated at reflux for 2 hours. The mixture was allowed to cool to ambient temperature, the precipitated solid was collected by filtration, washed with isopropanol and ether and dried to give 6,7-dimethoxy-4-(3-hydroxy-4-methylanilino)quinazoline hydrochloride (98 mg, 56%) as an off-white solid.

$^1$H NMR Spectrum: ($DMSOd_6$) 2.14(s, 3H); 3.98(s, 3H); 4.00(s, 3H); 6.97(d, 1H); 7.12(s, 1H); 7.14(d, 1H); 7.38(s, 1H); 8.27(s, 1H); 8.77(s, 1H); 9.65(br s, 1H)

MS-ESI: 312 [MH]$^+$

| Elemental analysis: | Found | C 59.1 | H 5.4 | N 11.8 |
|---|---|---|---|---|
| $C_{17}H_{17}N_3O_3$ 1HCl | Requires | C 58.6 | H 5.2 | N 12.1% |

EXAMPLE 14

A mixture of 4-chloro-6-methoxy-7-(2-methoxyethoxy)quinazoline (1 07 mg, 0.4 mmol) and 4-bromo-2-fluoroaniline (76 mg, 0.4 mmol) in isopropanol (7 ml) was heated at reflux for 2 hours. The mixture was allowed to cool to ambient temperature, the precipitated solid was collected by filtration, washed with isopropanol and ether and dried to give 4-(4-bromo-2-fluoroanilino)6-methoxy-7-(2-methoxyethoxy)quinazoline hydrochloride (151 mg, 82%) as an off-white solid.

m.p. 200–204° C.

$^1$H NMR Spectrum: ($DMSOd_6$; TFA) 3.36(s, 3H); 3.79(t, 2H); 4.02(s, 3H); 4.39(t, 2H); 7.37(s, 1H); 7.54–7.61(m, 2H); 7.81(dd, 1H); 8.16(s, 1H); 8.86(s, 1H)

MS-ESI: 422 [MH]$^+$

| Elemental analysis: | Found | C 47.56 | H 4.01 | N 9.29 |
|---|---|---|---|---|
| $C_{20}H_{21}N_3O_4BrF$ 0.95HCl | Requires | C 47.32 | H 3.96 | N 9.20% |

The starting material was prepared as follows:

A mixture of ethyl 4-hydroxy-3-methoxybenzoate (9.8 g, 50 mmol), 2-bromoethyl methyl ether (8.46 ml, 90 mmol) and potassium carbonate (12.42 g, 90 mmol) in acetone (60 ml) was heated at reflux for 30 hours. The mixture was allowed to cool and the solids removed by filtration. The volatiles were removed from the filtrate by evaporation and the residue triturated with hexane to give ethyl 3-methoxy-4-(2-methoxyethoxy)benzoate (11.3 g, 89%) as a white solid.

m.p. 57–60° C.

$^1$H NMR Spectrum: (DMSOd$_6$) 1.31(t, 3H); 3.29(s, 3H); 3.32(s, 3H); 3.68(m, 2H); 4.16(m, 2H); 4.28(q, 2H); 7.06(d, 1H); 7.45(d, 1H); 7.56(dd, 1H)

MS-FAB: 255 [MH]$^+$

Ethyl 3-methoxy-4-(2-methoxyethoxy)benzoate (9.5 g, 37 mmol) was added portionwise to stirred concentrated nitric acid (75 ml) at 0° C. The mixture was allowed to warm to ambient temperature and stirred for a further 90 minutes. The mixture was diluted with water and extracted with methylene chloride, dried (MgSO$_4$) and the solvent removed by evaporation. The residue was triturated with hexane to give ethyl 5-methoxy-4-(2-methoxyethoxy)-2-nitrobenzoate (10.6 g, 95%) as an orange solid.

m.p. 68–69° C.

$^1$H NMR Spectrum: (DMSOd$_6$) 1.27(t, 3H); 3.30(s, 3H); 3.69(m, 2H); 3.92(s, 3H); 4.25(m, 2H); 4.29(q, 2H); 7.30(s, 1H); 7.65(s, 1H)

MS-CI: 300 [MH]$^+$

A mixture of ethyl 5-methoxy-4-(2-methoxyethoxy)-2-nitrobenzoate (10.24 g, 34 mmol), cyclohexene (30 ml) and 10% palladium-on-charcoal catalyst (2.0 g) in methanol (150 ml) was heated at reflux for 5 hours. The reaction mixture was allowed to cool and diluted with methylene chloride. The catalyst was removed by filtration and the volatiles removed from the filtrate by evaporation. The residue was recrystallised from ethyl acetatelhexane to give ethyl 2-amino-5-methoxy-4-(2-methoxyethoxy) benzoate (8.0 g) as a buff solid. Formamide (80 ml) was added to this product and the mixture heated at 170° C. for 18 hours. About half the solvent was removed by evaporation under high vacuum and the residue was left to stand overnight. The solid product was collected by filtration, washed with ether and dried to give 6-methoxy-7-(2-methoxyethoxy)-3,4-dihydroquinazolin4-one (5.3 g, 62% over two steps) as a grey solid.

$^1$H NMR Spectrum: (DMSOd$_6$) 3.35(s, 3H); 3.74(m, 2H); 3.89(s, 3H); 4.26(m, 2H); 7.15(s, 1H); 7.47(s, 1H); 7.98(s, 1H); 12.03(br s, 1H)

MS-CI:251 [MH]$^+$

DMF (0.5 ml) was added to a mixture of 6-methoxy-7-(2-methoxyethoxy)-3,4-dihydroquinazolin4-one (5.1 g, 20 mmol) in thionyl chloride (50 ml). The mixture was stirred and heated at reflux for 3 hours, allowed to cool and the excess thionyl chloride removed by evaporation. The residue was suspended in methylene chloride and washed with aqueous sodium hydrogen carbonate solution. The aqueous phase was extracted with methylene chloride and the combined extracts dried (MgSO$_4$). The crude product was recrystallised from methylene chloride/hexane to give 4-chloro-6-methoxy-7-(2-methoxyethoxy)quinazoline (2.8 g, 51%) as a fine white solid.

$^1$H NMR Spectrum: (DMSOd$_6$) 3.37(s, 3H); 3.77(m, 2H); 4.0l(s, 3H); 4.37(m, 2H); 7.40(s, 1H); 7.49(s, 1H); 8.88(s, 1H)

MS-CI: 269 [MH]$^+$

EXAMPLE 15

A mixture of 4chloro-6-methoxy-7-(2-methoxyethoxy) quinazoline (107 mg, 0.4 mmol), (prepared as described for the starting material in Example 14), and 2-fluoro4-methylaniline (50 mg, 0.4 mmol) in isopropanol (7 ml) was heated at reflux for 2 hours. The mixture was allowed to cool to ambient temperature, the precipitated solid was collected by filtration, washed with isopropanol add ether and dried to give 4-(2-fluoro-4-methylanilino)-6-methoxy-7(2-methoxyethoxy)quinazoline hydrochloride (95 mg, 60%) as an off-white solid.

HPLC Characteristics:

Column—200×4.6 mm C18 ODS Hypersil (trade mark of Shandon) reversed phase 5 μm

Solvent—flow 1.5 ml/mm.

0–3 minutes: H$_2$O/CH$_3$CN (95/5) 0.001 M triethylamine

3–17 minutes: gradient H$_2$O/CH$_3$CN (95/5 to 5/95); constant 0.001M triethylamine Retention time: 10.46 minutes

EXAMPLE 16

A mixture of 4-chloro-7-(2-methoxyethoxy)quinazoline hydrochloride (450 mg, 1.6 mmol), (prepared as described for the starting material in Example 1), and 3-hydroxy4-methylaniline (280 mg, 2.27 mmol) in isopropanol (20 ml) was heated at reflux for 30 minutes. The solvent was removed by evaporation and the residue was triturated with isopropanol. The resulting solid was collected by filtration, washed with isopropanol and dried under vacuum to give 4-(3-hydroxy4-methylanilino)-7-(2-methoxyethoxy) quinazoline hydrochloride (428 mg, 74%).

$^1$H NMR Spectrum: (DMSOd$_6$) 2.18 (s, 3H); 3.38 (s, 3H); 3.8 (t, 2H); 4.35 (t, 2H); 7.05 (d, 1H); 7.15 (m, 2H); 7.35 (s, 1H); 7.52 (d, 1H); 8.75 (d, 1H); 8.85 (s, 1H); 9.7 (br s, 1H)

MS-ESI: 326 [MH]$^+$

| Elemental analysis: | Found | C 59.6 | H 5.8 | N 11.7 |
| C$_{13}$H$_{19}$N$_3$O$_3$ 1HCl | Requires | C 59.7 | H 5.5 | N 11.6% |

EXAMPLE 17

A solution of 1-(2-hydroxyethyl)4-methylpiperazine (112 mg, 0.78 mmol) in methylene chloride (1 ml) was added to a stirred suspension of 4-(4-chloro-2-fluoroanilino)-7-hydroxy-6-methoxy-quinazoline (225 mg, 0.7 mmol), (prepared as described for the starting material in Example 4), and tributylphosphine (420 mg, 2.1 mmol) in methylene chloride (10 ml). 1,1'-(Azodicarbonyl)dipiperidine (525 mg, 2.1 mmol) was then added in portions to the mixture. The resulting clear, pale yellow solution was stirred for 3.5 hours, then allowed to stand overnight. The reaction mixture was quenched with ether (8 ml) and the precipitate was removed by filtration. The solvent was removed from the filtrate by evaporation and the residue dissolved in acetone and treated with 1M ethereal hydrogen chloride until the hydrochloride salt precipitated. The precipitate was collected by filtration, dissolved in methanol and then basified with excess triethylamine. The volatiles were removed by evaporation and the residue purified by column chromatography eluting with methylene chloride/methanol/0.88 aqueous ammonia (100/8/1). The resulting purified oil was triturated with ether, collected by filtration and dried to give 4-(4-chloro-2-fluoroanilino)-6-methoxy 7-(2-(4-methylpiperazin-1-yl)ethoxy)quinazoline (79 mg, 25%) as a white solid.

m.p. 173–175° C.

$^1$H NMR Spectrum: (DMSOd$_6$) 2.10(s, 3H): 2.3(m, 4H); 2.5(m, 4H); 2.75(t, 2H): 3.95(s, 3H); 4.25(t, 2H); 7.21(s. 1H); 7.30(dd, 1H); 7.50(d, 1H); 7.55(dd, 1H); 7.75(s, 1H); 8.30(s, 1H); 9.50(s, 1H)

MS-ESI: 446 [MH]+

| Elemental analysis: | Found | C 59.1 | H 5.8 | N 15.5 |
|---|---|---|---|---|
| $C_{22}H_{25}N_5O_2FCl$ | Requires | C 59.3 | H 5.7 | N 15.7% |

The starting material was ptepared as follows:

2-Bromoethanol (2.36 g, 19 mmol) was added dropwise to a mixture of 1-methylpiperazine (1.26 g, 13 mmol) and potassium carbonate (5.0 g, 36 mmol) in absolute ethanol (150 ml) and the mixture heated at reflux for 18 hours. The mixture was allowed to cool and the precipitates were removed by filtration and the solvent volatiles were removed by evaporation. The residue was treated with acetone/methylene chloride, the insolubles were removed by filtration and the solvent was removed from the filtrate by evaporation to give 1-(2-hydroxyethyl)-4-methylpiperazine (870 mg, 48%) as a light brown oil.

$^1$H NMR Spectrum: ($CDCl_3$) 2.1 8(s, 3H); 2.3–2.7(br m, 8H); 2.56(t, 2H); 3.61 (t, 2H)

MS-ESI: 145 [MH]+

EXAMPLE 18

A solution of 4-chloro-6-methoxy-7-(3-morpholinopropoxy)quinazoline (2.5 g, 7.41 mmol) and 4-bromo-2-fluoroaniline (1.55 g, 8.15 mmol) in DMF (20 ml) was heated at 150° C. for 4 hours. The mixture was diluted with ether (200 ml) and the resulting precipitate collected by filtration. The solid was partitioned between methylene chloride and water and the aqueous phase was adjusted to pH8.5 with 1 M aqueous sodium hydroxide solution. The organic layer was separated, washed with brine, dried ($MgSO_4$) and the solvent removed by evaporation. The residue was purified by flash chromatography eluting with methylene chloride/methanol (9/1). The purified solid was dissolved in methanol and methylene chloride and 2.2 M ethereal hydrogen chloride (3 ml) was added. The volatiles were removed by evaporation, the residue was resuspended in ether, collected by filtration and dried under vacuum to give 4-(4-bromo-:2-fluoroanilino)-6-methoxy-7-(3-morpholinopropoxy)quinazoline hydrochloride (1.61 g, 26%).

$^1$H NMR Spectrum: ($DMSOd_6$; $CF_3COOD$) 2.3–2.4 (m, 2H); 3.15 (t, 2H); 3.34 (t, 2H); 3.54 (d, 2H); 3.76 (t, 2H); 4.02 (s, 3H); 4.04 (m, 2H); 4.33 (t, 2H); 7.41 (s, 1H); 7.5–7.65 (m, 2H); 7.80 (dd, 1H); 8.20 (s, 1H); 8.9 (s, 1H)

| Elemental analysis: | Found | C 46.5 | H 5.0 | N 9.9 |
|---|---|---|---|---|
| $C_{22}H_{24}N_4O_3BrF$ 0.4$H_2O$ 1.9HCl | Requires | C 46.5 | H 4.7 | N 9.9% |

The starting material was prepared as follows:

A mixture of 4-hydroxy-3-methoxybenzoic acid (4.5 g, 26.8 mmol), 3-morpholinopropyl chloride (9.5 g, 58.0 mmol), (prepared according to J. Am. Chem. Soc. 1945, 67, 736), potassium carbonate (8.0 g, 58 mmol), potassium iodide (1.0 g, 0.22 mmol) and DMF (80 ml) was stirred and heated at 100° C. for 3 hours. The solid was removed by filtration and the filtrate evaporated. The residue was dissolved in ethanol (50 ml), 2 M sodium hydroxide (50 ml) was added and the mixture heated at 90° C. for 2 hours. After partial evaporation, the mixture was acidified with concentrated hydrochloric acid, washed with ether and then subjected to purification on a Diaion (trade mark of Mitsubishi) HP20SS resin column, eluting with water and then with a gradient of methanol (0 to 25%) in hydrochloric acid (pH2). Partial evaporation of the solvents and lyophilisation gave 3-methoxy-4-(3-morpholinopropoxy)benzoic acid (8.65 g, 97%).

$^1$H NMR Spectrum: ($DMSOd_6$; T1FA) 2.17–2.24(m, 2H); 3.10–3.16(m, 2H); 3.30(t, 2H); 3.52(d, 2H); 3.71(t, 2H); 3.82(s, 3H); 4.01(br d, 2H); 4.14(t, 2H); 7.08(d, 1H); 7.48(d, 1H); 7.59(dd, 1H)

MS-ESI: 296 [MH]+

Fuming nitric acid (1.5 ml, 36.2 mmol) was added slowly at 0° C. to a solution of 3-methoxy-4-(3-morpholinopropoxy)benzoic acid (7.78 g, 23.5 mmol) in TFA (25 ml). The cooling bath was removed and the reaction mixture stirred at ambient temperature for 1 hour. The TFA was removed by evaporation and ice was added to the residue. The precipitate was collected by filtration; washed with a minimum of water followed by toluene and ether. The solid was dried under vacuum over phosphorus pentoxide to give 5-methoxy-4-(3-morpholinopropoxy)-2-nitroblenzoic acid (7.54 g) which was used without further purification.

$^1$H NMR Spectrum: ($DMSOd_6$; TFA) 2.16–2.23(m, 2H); 3.10–3.17(m, 2H); 3.30(t, 2H); 3.52(d, 2H); 3.66(t, 2H); 3.93(s, 3H); 4.02(brd, 2H); 4.23(t, 2H); 7.34(s, 1H); 7.61(s, 1H)

MS-EI: 340 [M]+

Thionyl chloride (15 ml) and DMF (0.05 ml) were added to 5-methoxy-4-(3-morpholinopropoxy)-2-nitrobenzoic acid (7.54 g). The mixture was heated at 50° C. for 1 hour, the excess thionyl chloride was removed by evaporation and by azeotroping with toluene (x2). The resulting solid was suspended in THF (200 ml) and ammonia was bubbled through the mixture for 30 minutes. The precipitate was removed by filtration and washed with THF. After concentration of the filtrate by evaporation, the product crystallised and was collected by filtration to give 5-methoxy-4-(3-morpholinopropoxy)-2-nitrobenzamide (5.25 g) as light yellow crystals which were used without further purification.

$^1$H NMR Spectrum: ($DMSOd_6$; TFA) 2.17–2.24(m, 2H); 3.11–3.18(m, 2H); 3.31(t, 2H); 3.53(d, 2H); 3.67(t, 2H); 3.93(s, 3H); 4.03(brd, 2H); 4.21(t, 2H); 7.17(s, 1H); 7.62(s, 1H)

MS-EI: 339 [M]+

Concentrated hydrochloric acid (30 ml) was added to a suspension of 5-methoxy-4-(3-morpholinopropoxy)-2-nitrobenzamide (5.67 g) in methanol (150 ml) and the mixture was heated to 60° C. When the 5-methoxy-4-(3-morpholinopropoxy)-2-nitrobenzamide had dissolved, iron powder (5.6 g, 100 mmol) was added in portions to the reaction mixture which was then heated for 90 minutes. After cooling, the insolubles were removed by filtration through diatomaceous earth, the volatiles were removed from the filtrate by evaporation and the residue was purified on a Diaion (trade mark of Mitsubishi) HP20SS resin column, eluting with water and then with hydrochloric acid (pH2). Concentration of the fractions by evaporation gave a precipitate which was collected by filtration and dried under vacuum over phosphorus pentoxide to give 2-amino-5-methoxy-4-(3-morpholinopropoxy)benzamide as a hydrochloride salt (4.67 g, 75%) as beige crystals.

$^1$H NMR Spectrum: ($DMSOd_6$; TFA) 2.22–2.28(m, 2H); 3.12(br t, 2H); 3.29(t, 2H); 3.51(d, 2H); 3.75(t, 2H); 3.87(s, 3H); 4.00(br d, 2H); 4.12(t, 2H); 7.06(s, 1H); 7.53(s, 1H)

MS-EI: 309 [M]+

A mixture of 2-amino-5-methoxy4-(3-morpholinopropoxy)benzamide (4.57 g, 12.25 mmol) and Gold's reagent (2.6 g, 15.89 mmol) in dioxane (35 ml) was heated at reflux for 5 hours. Acetic acid (0.55 ml) and sodium acetate (1.0 g) were added to the reaction mixture which was heated for a further 3 hours. The mixture was cooled to ambient temperature and the volatiles removed by evaporation. The residue was adjusted to pH7 with 2 M sodium hydroxide and then purified on a Diaion (trade mark of Mitsubishi) HP20SS resin column, eluting with methanol (gradient of 0 to 60%) in water. Concentration of the fractions by evaporation gave a precipitate which was collected by filtration and dried under vacuum over phosphorus pentoxide to give 6-methoxy-7-(3-morpholinopropoxy)-3,4-dihydroquinazolin-4-one (3.04 g, 78%) as a white solid.

$^1$H NMR Spectrum: (CDCl$_3$) 2.10(q, 2H); 2.48(m, 4H); 2.56(t, 2H); 3.72(t, 4H); 4.00(s, 3H); 4.24(t, 2H); 7.18(s, 1H); 7.60(s, 1H); 8.00(s, 1H); 10.86(br s, 1H)

MS-EI: 319 [M]$^+$

A mixture of 6-methoxy-7-(3-morpholinopropoxy)-3,4-dihydroquinazolin-4-one (638 mg, 2 mmol) and thionyl chloride (8 ml) was heated at reflux for 30 minutes. Excess thionyl chloride was removed by evaporation and by azeotroping with toluene (x2). The residue was suspended in methylene chloride and 10% aqueous solution of sodium hydrogen carbonate was added to the mixture. The organic layer was separated, dried (MgSO$_4$) and the solvent removed by evaporation. The residue was triturated with ether, the solid was collected by filtration, washed with ether and dried under vacuum to give 4-chloro-6-methoxy-7-(3-morpholinopropoxy)quinazoline (590 mg, 87%).

$^1$H NMR Spectrum: (CDCl$_3$) 2.110–2.16(m, 2H); 2.48(br s, 4H); 2.57(t, 2H); 3.73(t, 4H); 4.05(s, 3H); 4.29(t, 2H); 7.36(s, 1H); 7.39(s, 1H); 8.86(s, 1H)

MS-ESI: 337 [MH]$^+$

EXAMPLE 19

A mixture of 4-chloro-7-(3-morpholinopropoxy) quinazoline hydrochloride (238 mg, 0.69 mmol) and 4-chloro-2-fluoroaniline (145 mg, 1 mmol) in isopropanol (5 ml) was heated at reflux for 1 hour. The solvent was removed by evaporation and the residue partitioned between water and ethyl acetate and the aqueous layer adjusted to pH8 with sodium hydrogen carbonate. The organic layer was separated, washed with brine, dried (MgSO$_4$) and the solvent removed by evaporation. The residue was purified by flash chromatography eluting with methylene chloride/acetonitrile/methanol (60/30/10 followed by 60/20/20). The resulting semi-purified solid was repurified by chromatography on neutral alumina eluting with methylene chloridel-metlhanol (95/5). The resulting white solid was dissolved in methylene chloride and 4 M ethereal hydrogen chloride (0.5 ml) was added. The volatiles were removed by evaporation, and the residue triturated by the addition of methylene chloride followed by methanol and ether. The precipitated solid was collected by filtration and dried under vacuum to give 4-(4-chloro-2-fluoroanilino)-7-(3-morpholinopropoxy) quinazoline hydrochloride (35 mg, 10%).

$^1$H NMR Spectrum: (DMSOd$_6$; CF$_3$COOD) 2.3(m, 2H); 3.13(t, 2H); 3.34(t, 2H); 3.52(d, 2H); 3.68(t, 2H); 4.01(d, 2H); 4.34(t, 2H); 7.37(s, 1H); 7.46(d, 1H); 7.54(dd. 1H); 7.61(t, 1H); 7.71(d, 1H); 8.71(d, 1H); 8.93(s, 1H)

MS-ESI: 417 [MH]$^+$

| Elemental analysis: | Found | C 50.9 | H 5.2 | N 11.5 |
|---|---|---|---|---|
| C$_{21}$H$_{22}$N$_4$O$_2$ClF 0.8H$_2$O 1.75HCl | Requires | C 50.9 | H 5.2 | N 11.3% |

The starting material was prepared as follows:

Sodium metal (2.2 g, 95 mmol) was added carefully to benzyl alcohol (50 ml) at ambient temperature. The mixture was stirred for 30 minutes at ambient temperature and then heated at 80° C. for 1 hour. The mixture was allowed to cool to 40° C. and 7-fluoro-3,4-dihydroquinazolin-4-one (3.9 g, 24 mmol), (prepared as described for the starting material in Example 1), was added. The reaction mixture was then stirred and heated at 130° C. for 4 hours and left to cool to ambient temperature overnight. The mixture was quenched with water, the resulting precipitate wvas triturated by the addition of ether (150 ml), collected by filtration and dried for 4 hours at 60° C. under high vacuum to give 7-benzyloxy-3,4-dihydroquinazolin-4-one (5.33 g, 89%).

7-Benzyloxy-3,4-dihydroquinazolin-4-one (5.3 g, 21 mmol) was suspended in dry DMF (50 ml) and sodium hydride (1 g of a 60% suspension in mineral oil, 25 mmol) was added. After hydrogen evolution had ceased, the reaction was allowed to cool to ambient temperature and then chloromethyl pivalate (4.1 g, 27 mmol) was added dropwise over 10 minutes. The mixture was stirred for 30 minutes then poured into aqueous citric acid solution (pH5) (250 ml) and extracted with ether (3×300 ml). The combined extracts were washed with brine, dried (MgSO$_4$) and the solvent removed by evaporation. The resulting solid was triturated with isohexane, collected by filtration and dried under vacuum to give 7-benzyloxy-3-methylpivaloyl-3,4-dihydroquinazolin-4-one (6.9 g, 90%).

5% Palladium-on-charcoal catalyst (0.7 g, 50% in water) was added to a solution of 7-benzyloxy-3-methylpivaloyl-3,4-dihydroquinazolin-4-one (6.85 g, 18.7 mmol) in ethyl acetate (300 ml), methanol (40 ml), DMF (40 ml), and acetic acid (0.7 ml). The mixture was vigorously stirred under hydrogen at atmospheric pressure for 4.5 hours. The catalyst was removed by filtration through diatomaceous earth, the filtrate concentrated by evaporation to about 60 ml, diluted with water (300 ml) and extracted with ether (3×300 ml). The combined extracts were washed with brine, dried (MgSO$_4$), and the volatiles removed by evaporation. The resulting crude solid was dissolved in acetone (200 ml) and acetic acid (0.2 ml) and cooled to 0° C. Potassium permanganate (1.8 g) was added and the mixture stirred for 10 minutes. The reaction mixture was poured into water (250 ml) and ethyl acetate (250 ml) was added. The precipitate was removed ;by filtration, the organic phase separated and the aqueous phase re-extracted with ethyl acetate (2×100 ml). The combined extracts were washed with water and brine, dried (MgSO$_4$) and the volatiles removed by evaporation to give 7-hydroxy-3-methylpivaloyl-3,4-dihydroquinazolin-4-one (4.05 g, 78%) as a cream solid.

7-hydroxy-3-methylpivaloyl-3,4-dihydroquinazolin-4-one (750mg, 2.7 mmol) was suspended in methylene chloride (40 ml) and 4-(3-hydroxypropyl)morpholine (490 mg, 3.4 mmol) and triphenylphosphine (890 mg, 3.4 mmol) were added at 5° C. The mixture was stirred for 5 minutes at 5° C. and diethyl azodicarboxylate (590 mg, 3.4 mmol) was added over 5 minutes. The reaction mixture was stirred at 5° C. for 30 minutes then at ambient temperature for 1 hour. The reaction mixture was purified directly by column chromatography eluting with methylene chloride, then ethyl acetate, then acetonitrile/ethyl acetate (1/5), and finally acetonitrile/ethyl acetate/aqueous ammonia (50/50/0.5). The purified product was triturated with ether/isohexane and collected by filtration to give 3-methylpivaloyl-7-(3-morpholinopropoxy)-3,4-dihydroquinazolin-4-one (745 mg, 68%).

A solution of 3-methylpivaloyl-7-(3-morpholinopropoxy)-3,4-dihydroquinazolin-4-one (680 mg, 1.6 mmol) in saturated methanolic ammonia (20 ml) was stirred at 40° C. for 6 hours then for 18 hours at ambient temperature. The solvent was removed by evaporation and the residue was triturated with ether/isohexane. The resulting solid was collected by filtration to give 7-(3-morpholinopropoxy)-3,4-dihydrwquinazolina-one (450 mg, 92%) as a white solid.

$^1$H NMR Spectrum: (DMSOd$_6$) 1.9(m, 2H); 2.35(t, 4H); 2.4(t, 2H); 3.55(t, 4H); 4.15(t, 2H); 7.05(m, 2H); 7.97(d, 1H); 8.02(s, 1H)

MS-ESI: 290 [MH]$^+$

A mixture of 7-(3-morpholinopropoxy)-3,4-dihydroquinazolin-4-one (200 mg, 0.69 mmol) in thionyl chloride (5 ml) and DMF (0.1 ml) was heated at reflux for 1 hour. The solution was diluted with toluene and the volatiles removed by evaporation. The residue was dissolved in methylene chloride and ether was added. The resulting precipitate was collected by filtration, washed with ether and dried under vacuum to give 4-chloro-7-(3-morpholinopropoxy)quinazoline hydrochloride (238 mg, 100%).

The 4-(3-hydroxypropyl)morpholine was prepared as follows:

Morpholine (94 g, 1.08 mol) was added dropwise to a solution of 3-bromo-1-propanol (75 g, 0.54 mol) in toluene (750 ml) and the reaction then heated at 80° C. for 4 hours. The mixture was allowed to cool to ambient temperature and the precipitated solid was removed by filtration. The volatiles were removed from the filtrate and the resulting yellow oil was purified by distillation at 0.4–0.7 mmHg to give 4-(3-hydroxypropyl)morpholine (40 g, 50%) as a colourless oil.

b.p. 68–70° C. (~0.5 mmHg)

$^1$H NMR Spectrum: (DMSOd$_6$) 1.65–1.78(m, 2H); 2.50(t, 4H); 2.60(t, 2H); 3.68(t, 4H); 3.78(t, 2H); 4.90(br d, 1H)

EXAMPLE 20

5M Isopropanolic hydrogen chloride (1.5 ml) was added to a solution of 4-chloro-6-methoxy-7-(3-morpholinopropoxy)quinazoline (202 mg, 0.6 mmol), (prepared as described for the starting material in Example 18), and 4-cyano-2-fluoroaniline (100 mg, 0.72 mmol), (U.S. Pat. No. 4,120,693), in isopropanol (5 ml) heated at 50° C. The mixture was then heated at 80° C. for 2 hours, allowed to cool to ambient temperature and left standing overnight. The resulting precipitate was collected by filtration and the solid was then partitioned between methylene chloride and water and 1M aqueous sodium hydroxide solution (0.8 ml) was added. The organic layer was separated, washed with brine, dried (MgSO$_4$) and the solvent removed by evaporation. The residue was purified by flash chromatography eluting with methylene chloride/methanol (94/6). The purified solid was dissolved in methylene chloride and 2.2M ethereal hydrogen chloride was added. The precipitated product was collected by filtration, washed with ether and dried under vacuum to give $^4$-(4-cyano-2-fluoroanilino)-6-methoxy 7-(3-morpholinopropoxy)quinazoline hydrochloride (125 mg, 39%).

$^1$H NMR Spectrum: (DMSOd$_6$; CF$_3$COOD) 2.3–2.4(m, 2H); 3.15(t, 2H); 3.36(t, 2H); 3.54(d, 2H); 3.75(t, 2H); 4.02(d, 2H); 4.04(s, 3H); 4.34(t, 2H); 7.44(s, 1H); 7.8–7.9 (m, 2H); 8.11(d. 1H); 8.25(s, 1H); 8.94(s, 1H)

| Elemental analysis: | Found | C 52.7 | H 5.4 | N 12.9 |
|---|---|---|---|---|
| C$_{23}$H$_{24}$N$_5$O$_3$F 0.5H$_2$O 1.9HCl 0.07 ether 0.15 methylene chloride | Requires | C 52.7 | H 5.3 | N 13.1% |

EXAMPLE 21

Diethyl azodicarboxylate (123 μl, 0.88 mmol) was added portionwise to a mixture of 4-(4-chloro-2-fluoroanilino)-7-hydroxy-6-methoxyquinazoline (250 mg, 0.8 mmol), (prepared as described for the starting material in Example 4), triphenylphosphine (228 mg, 0.96 mmol) and 3-methoxy-1-propanol (71 mg, 0.8 mmol) in methylene chloride (20 ml) cooled at 0° C. The mixture was then allowed to warm to ambient temperature and stirred for 18 hours. The resulting precipitate was removed by filtration and the solvent removed from the filtrate by evaporation. The residue was purified by column chromatography eluting with methylene chloride/methanol/concentrated aqueous ammonia (100/8/1). The purified oil was treated with ethereal hydrogen chloride and the volatiles were then removed by evaporation. The residue was triturated with ether and the solid collected by filtration to give 4-(4-chloro-2-fluoroanilino)-6-methoxy-7-(3-methoxypropoxy) quinazoline hydrochloride (100 mg, 32%) as a yellow solid.

$^1$H NMR Spectrum: (DMSOd$_6$) 2.10(m, 2H); 3.25(s, 3H); 3.5(t, 2H); 4.00(s, 3H); 4.25(t, 2H); 7.4(s, 1H); 7.45(dd, 1H); 7.60(m, 2H); 8.25(s, 1H); 8.8(s, 1H); 11.5(s, 1H)

MS-ESI: 392 [MH]$^+$

| Elemental analysis: | Found | C 52.7 | H 4.4 | N 10.1 |
|---|---|---|---|---|
| C$_{19}$H$_{19}$N$_3$O$_3$FCl 0.1H$_2$O 1HCl | Requires | C 53.1 | H 4.7 | N 9.8% |

EXAMPLE 22

Diethyl azodicarboxylate (123 μl, 0.88 mmol) was added portionwise to a mixture of 4-(4-chloro-2-fluoroanilino)-7-hydroxy-6-methoxyquinazoline (250 mg, 0.8 mmol), (prepared as described for the starting material in Example 4), triphenylphosphine (228 mg, 0.96 mmol) and 2-ethoxyethanol (71 μl, 0.8 mmol) in methylene chloride (20 ml) cooled at 0° C. The mixture was then allowed to warm to ambient temperature and stirred for 18 hours. The resulting precipitate was removed by filtration and the solvent removed from the filtrate by evaporation. The residue was purified by chromatography eluting with methylene chloride/methanol (96/4). The resulting purified oil was dissolved in acetone and treated with water (80 μl) then ethereal hydrogen chloride. The resulting granular solid was collected by filtration to give 4-(4-chloro-2-fluoroanilino)-6-methoxy-7-(2-ethoxyethoxy)quinazoline hydrochloride (96 mg, 31%).

$^1$H NMR Spectrum: (DMSOd$_6$) 1.15(t, 3H); 3.50(q, 2H); 3.8(t, 2H); 4.00(s, 3H); 4.30(t, 2H); 7.35(s, 1H); 7.40(dd, 1H); 7.60(dd, 1H); 7.65(dd 1H); 8.25(s, 1H); 8.8(s, 1H); 11.53(s, 1H)

MS-ESI: 392 [MH]+

| Elemental analysis: | Found | C 53.2 | H 4.6 | N 10.1 |
|---|---|---|---|---|
| $C_{19}H_{19}N_3O_3FCl$ 1HCl | Requires | C 53.28 | H 4.71 | N 9.81% |

EXAMPLE 23

Lithium borohydride (150 μl of a 2M solution in THF, 0.15 mmol) was added to a solution of 4-(4-chloro-2-fluoroanilino)-7-(ethoxycarbonylmethoxy)-6-methoxyquinazoline (150 mg, 0.3 mmol) in THF (1 ml) and the mixture stirred for 1.5 hours. The reaction mixture was quenched with aqueous amonium chloride solution and extracted with ethyl acetate. The combined extracts were washed with water, dried ($MgSO_4$) and concentrated by evaporation. Hexane was added, the mixture was cooled and the precipitated solid was collected by filtration to give 4-(4-chloro-2-fluoroanilino)-7-(2-hydroxyethoxy)-6-methoxyquinazoline (30 mg, 23%).

$^1$H NMR Spectrum: ($DMSOd_6$) 3.82(t, 2H); 3.98(s, 3H); 4.18(t, 2H); 4.92(t, 1H); 7.20(dd, 1H); 7.54–7.63(m, 2H); 7.72(s, 1H); 7.92(s, 1H); 8.60(s, 1H)

MS-ESI: 364 [MH]+

The starting material was prepared as follows:

A mixture of 4-(4-chloro-2-fluoroanilino)-7-hydroxy-6-methoxyquinazoline (3.0 g, 9 mmol), (prepared as described for the starting material in Example 4), ethyl bromoacetate (1.11 ml, 10 mmol) and potassium carbonate (2.84 g, 20.6 mmol) in NMP (60 ml) was heated at 90° C. for 3 hours. The mixture was allowed to cool, diluted with water and extracted with ethyl acetate. The combined extracts were washed with water, dried ($MgSO_4$) and concentrated by evaporation. Hexane was added, the mixture was cooled and the precipitated solid was collected by filtration to give 4-(4-chloro-2-fluoroanilino)-7-(ethoxycarbonylmethoxy)-6-methoxyquinazoline (1.75 g, 48%).

$^1$H NMR Spectrum: ($DMSOd_6$) 1.20(t, 3H); 3.95(s, 3H); 4.18(q, 2H); 4.98(s, 2H); 7.08(s, 1H); 7.30(dd. 1H); 7.48–7.58(m, 2H); 7.82(s, 1H); 8.34(s, 1H); 9.57(s, 1H)

EXAMPLE 24

Diethyl azodicarboxylate (209 mg, 1.2 mmol) was added dropwise to a suspension of 4-(4-bromo-2-fluoroanilino)-7-hydroxy-6-methoxyquinazoline (146 mg, 0.4 mmol), triphenylphosphine (314 mg, 1.2 mmol) and 1-(2-hydroxyethyl) 4-methylpiperazine (86 mg, 0.6 mmol), (prepared as described for the starting material in Example 17), in methylene chloride (5 ml). The mixture was stirred for 1 hour at ambient temperature and the mixture was purified by column chrormatography eluting with methylene chloride/methanol (90/10 followed by 80/20). The purified product was triturated with ether, collected by filtration and dried under vacuum. The solid was dissolved in methylene chloride and 3M ethereal hydrogen chloride (0.5 ml) was added. The volatiles were removed by evaporation and the resulting oil was triturated with ether. The solid was collected by filtration, washed with ether and dried under vacuum to give 4-(4-bromo-2-fluoroanilino)-6-methoxy-7-(2-(4-methylpiperazin-1-yl)ethoxy)quinazoline hydrochloride (100 mg, 41%).

$^1$H NMR Spectrum: ($DMSOd_6$; $CF_3COOD$; 60° C.) 2.89 (s, 3H); 3.55–3.7(m, 8H); 3.74(t, 2H); 4.04(s, 3H); 4.68(t, 2H); 7.49(s, 1H); 7.55(m, 1H); 7.56(s, 1H); 7.75(d, 1H); 8.29(s, 1H); 8.84(s, 1H)

MS-EI: 490 [M]+

| Elemental analysis: | Found | C 43.9 | H 5.1 | N 11.0 |
|---|---|---|---|---|
| $C_{22}H_{25}N_5O_2BrF$ 1$H_2O$ 2.7HCl 0.2ether | Requires | C 44.0 | H 5.1 | N 11.3% |

The starting material was prepared as follows:

A solution of 7-benzyloxy-4-chloro-6-methoxyquinazoline hydrochloride (8.35 g, 24.8 mmol), (prepared as described for the starting material in Example 4), and 4-bromo-2 fluoroaniline (5.65 g, 29.7 mmol) in isopropanol (200 ml) was heated at reflux for 4 hours. The resulting precipitated solid was collected by filtration, washed with isopropanol and then ether and dried under vacuum to give 7-benzyloxy4-(4-bromo-2-fluoroanilino)-6-methoxyquinazoline hydrochloride (9.46 g, 78%).

$^1$H NMR Spectrum: ($DMSOd_6$; $CD_3COOD$) 4.0(s, 3H); 5.37(s, 2H); 7.35–7.5(m, 4H); 7.52–7.62(m, 4H); 7.8(d, 1H); 8.14(9s, 1H); 8.79(s, 1H)

MS-ESI: 456 [MH]+

| Elemental analysis: | Found | C 54.0 | H 3.7 | N 8.7 |
|---|---|---|---|---|
| $C_{22}H_{17}O_2N_3BrF$ 0.9HCl | Requires | C 54.2 | H 3.7 | N 8.6% |

A solution of 7-benzyloxy-4-(4-bromo-2-fluoroanilino)-6-methoxyquinazoline hydrochloride (9.4 g, 19.1 mmol) in TFA (90 ml) was heated at reflux for 50 minutes. The mixture was allowed to cool aid was poured on to ice. The resulting precipitate was collected by filtration and dissolved in methanol (70 ml). The solution was adjusted to pH9–10 with concentrated aqueous ammonia solution. The mixture was concentrated to half initial volume by evaporation. The resulting precipitate was collected by filtration, washed with water and then ether, and dried under vacuum to give 4-(4-bromo-2-fluoroanilino)-7-hydroxy-6-methoxyquinazoline (5.66 g, 82%).

$^1$H NMR Spectrum: ($DMSOd_6$; $CD_3COOD$) 3.95(s, 3H); 7.09(s, 1H); 7.48(s, 1H); 7.54(t, 1H); 7.64(d, 1H); 7.79(s, 1H); 8.31(s, 1H)

MS-ESI: 366 [MH]+

| Elemental analysis: | Found | C 49.5 | H 3.1 | N 11.3 |
|---|---|---|---|---|
| $C_{15}H_{11}O_2N_3BrF$ | Requires | C 49.5 | H 3.0 | N 11.5% |

EXAMPLE 25

Diethyl azodicarboxylate (209 mg, 1.2 mmol) was added dropwise to a suspension of 4-(4-bromo-2-fluoroanilino)-7-hydroxy-6-methoxyquinazoline (146 mg, 0.4 mmol), (prepared as described for the starting material in Example 24), triphenylphosphine (314 mg, 1.2 mmol) and 4-(2-hydroxyethyl)morpholine (79 mg, 0.6 mmol) in methylene chloride (5 ml). The mixture was stirred for 1 hour at ambient temperature and purified by column flash chromatography eluting with methylene chloride/methanol (95/5 followed by 90/10) to give a white solid. The solid was dissolved in methylene chloride/methanol and 2M ethereal hydrogen chloride (0.5 ml) was added. The mixture was concentrated by evaporation and the resulting precipitate was collected by filtration, washed with ether and dried under vacuum to give 4-(4-bromo-2-fluoroanilino)-6-methoxy-7-(2-morpholinoethoxy)quinazoline hydrochloride (155 mg, 70%).

¹H NMR Spectrum: (DMSOd₆; CF₃COOD) 3.3(t, 2H); 3.6(d, 2H); 3.75(m, 2H); 3.8(m, 2H); 4.0(m, 2H); 4.03(s, 3H); 4.7(t, 2H); 7.5(s, 1H); 7.55–7.65(m, 2H); 7.8(d, 1H); 8.26(s, 1H); 8.9(s, 1H)

MS-EI: 477 [M.]⁺

| Elemental analysis: | Found | C 45.3 | H 4.5 | N 9.8 |
|---|---|---|---|---|
| C₂₁H₂₂N₄O₃BrF 0.4H₂O 2.0HCl | Requires | C 45.2 | H 4.5 | N 10.0% |

EXAMPLE 26

A solution of 7-(4-chlorobutoxy)4-(4-chloro-2-fluoroanilino)-6-methoxyquinazoline (3.64 g, 8.87 mmol) in morpholine (70 ml) was heated at 110° C. for 2 hours. The mixture was allowed to cool and was partitioned between ethyl acetate and water. The organic layer was separated, washed with brine, dried (MgSO₄) and the volatiles removed by evaporation. The residue was purified by column chromatography eluting with methylene chloride and methanol (92/8). The purified solid product was dissolved in methylene chloride and 3M ethereal hydrogen chloride was added. The volatiles were removed by evaporation, and the residue triturated with ether. The solid was collected by filtration, washed with ether and dried under vacuum at 60° C. to give 4-(4-chloro-2-fluoroanilino)-6-methoxy-7-(4-morpholinobutoxy)quinazoline hydrochloride (3.8 g, 78%).

¹H NMR Spectrum: (DMSOd₆; CF₃COOD) 1.85–2.0(m, 4H); 3.09(t, 2H); 3.2–3.3(t, 2H); 3.46(d, 2H); 3.74(t, 2H); 4.0(d, 2H); 4.03(s, 3H); 4.27(s, 2H); 7.42(s, 1H); 7.46(d, 1H); 7.63(t, 1H); 7.68(d, 1H); 8.21(s, 1H); 3.88(s, 1H)

MS-ESI: 461 [MH]⁺

| Elemental analysis: | Found | C 50.8 | H 5.3 | N 10.0 |
|---|---|---|---|---|
| C₂₃H₂₆N₄O₃ClF 1.95HCl 0.6H₂O 0.08ether | Requires | C 51.0 | H 5.5 | N 10.2% |

The starting material was prepared as follows:

A mixture of 4-(4-chloro-2-fluoroanilino)-7-hydroxy-6-methoxyquinazoline (3.6 g, 11.3 mmol), (prepared as described for the starting material in Example 4), 1 bromo-4-chlorobutane (1.95 ml, 16.9 mmol) and potassium carbonate (4.66 g, 33.8 mmol) in DMF (75 ml) was heated at 40° C. for 4 hours. The mixture was allowed to cool and was partitioned between methylene chloride and water. The aqueous layer was adjusted to pH7 with 2M hydrochloric acid. The organic layer was separated, washed with brine, dried (MgSO₄) and the volatiles removed by evaporation. The residue was purified by column chromatography eluting with methylene chloride/ethyl acetate (1/1). The purified solid product was triturated with pentane, collected by filtration and dried under vacuum to give 7-(4-chlorobutoxy)-4(4chloro-2-fluoroanilino)-6-methoxyquinazoline (3.64 g, 79%).

¹H NMR Spectrum: (DMSOd₆; CF₃COOD) 1.9–2.1(m, 4H); 3.76(t, 2H); 4. 01(s, 3H); 4.2%(t, 2H); 7.33(s, 1H); 7.46(d, 1H); 7.63(t, 1H); 7.70(d, 1H); 8.08(s, 1H); 8.88(s, 1H)

EXAMPLE 27

A suspension of 4-(4-chloro-2-fluoroanilino)-7-(3-chloropropoxy)-6-methoxyquinaneoline (150 mg, 0.3 mmol) in 1-methylpiperazine (2 ml) was heated at 100° C. for 3 hours. The mixture was allowed to cool and was partitioned between aqueous sodium carbonate solution pH11.5) and ethyl acetate. The organic layer was separated, washed with brine, dried (MgSO₄) and the volatiles removed by evaporation. The residue was dissolved in methylene chloride and ether was added. The resulting precipitate was collected by filtration washed with ether and dried. The solid was dissolved in methylene chloride and 2.2M ethereal hydrogen chloride (1 ml) was added. After concentrating to half of initial volume, the resulting precipitate was collected by filtration, washed with ether and dried under vacuum to give 4-(4-chloro-2-fluoroanilino)-6-methoxy-7-(3-(4-methylpiperazin-1-yl)propoxy) quinazoline hydrochloride (158 mg, 75%).

¹HNMR Spectrum: (DMSOd₆; CF₃COOD; 60° C.) 2.35 (m, 2H); 2.95(s, 3H); 3.43(t, 2H); 3.52–3.7(m, 8H); 4.03(s, 3H); 4.34(t, 2H); 7.41 (s, 1H); 7.45(d, 1H); 7.6–7.7(m, 2H); 8.1 1 (s, 1H); 8.8(s, 1H)

MS-EI: 460 [MH]⁺

| Elemental analysis: | Found | C 48.6 | H 5.6 | N 11.9 |
|---|---|---|---|---|
| C₂₃H₂₇N₅O₂FCl 0.7H₂O 2.75HCl | Requires | C 48.2 | H 5.5 | N 12.2% |

The starting material was prepared as follows:

A mixture of 4-(4-chloro-2-fluoroanilino)-7-hydroxy-6-methoxyquinazoline (957 mg, 3 mmol), (prepared as described for the starting material in Example 4). 1-bromo-3-chloropropane (2.36 g, 15 mmol) and potassium carbonate (2.1 g, 15 mmol) in DMF (20 ml) was heated at 40° C. for 1.5 hours. The mixture was allowed to cool, was diluted with water and extracted with ethyl acetate (3×50 ml). The organic extracts were combined, washed with water and brine, dried (MgSO₄) and the volatiles were removed by evaporation. The residue was triturated with hexane/ethyl acetate, collected by filtration and dried under vacuum to give 4-(4-chloro-2-fluoroanilino)-7-(3-chloropropoxy)-6-methoxyquinazolsine (650 mg, 55%).

¹H NMR Spectrum: (DMSOd₆) 2.26(m, 21); 3.82(t, 2H); 3.95(s, s 3H); 4.26(t, 2H); 7.20(s, 3H); 7.32(dd, (H); 7.48–7.60(m, 2H); 7.80(s, 1H); 8.35(s, 1H); 9.52(s, 2H)

MS-EI: 396 [MH]⁺

EXAMPLE 28

The following illustrate representative pharmaceutical dosage forms containing the compound of formula I, or a pharmaceutically acceptable salt thereof (hereafter compound X), for therapeutic or prophylactic use in humans:

| (a) | Tablet I | mg/tablet |
|---|---|---|
|  | Compound X | 100 |
|  | Lactose Ph.Eur | 182.75 |
|  | Croscarmellose sodium | 12.0 |
|  | Maize starch paste (5% w/v paste) | 2.25 |
|  | Magnesium stearate | 3.0 |
| (b) | Tablet II | mg/tablet |
|  | Compound X | 50 |
|  | Lactose Ph.Eur | 223.75 |
|  | Croscarmellose sodium | 6.0 |

-continued

| | | |
|---|---|---|
| | Maize starch | 15.0 |
| | Polyvinylpyrrolidone (5% w/v paste) | 2.25 |
| | Magnesium stearate | 3.0 |
| (c) | Tablet III | mg/tablet |
| | Compound X | 1.0 |
| | Lactose Ph.Eur | 93.25 |
| | Croscarmellose sodium | 4.0 |
| | Maize starch paste (5% w/v paste) | 0.75 |
| | Magnesium stearate | 1.0 |
| (d) | Capsule | mg/capsule |
| | Compound X | 10 |
| | Lactose Ph.Eur | 488.5 |
| | Magnesium stearate | 1.5 |
| (e) | Injection I | (50 mg/ml) |
| | Compound X | 5.0% w/v |
| | 1N Sodium hydroxide solution | 15.0% v/v |
| | 0.1N Hydrochloric acid | |
| | (to adjust pH to 7.6) | |
| | Polyethylene glycol 400 | 4.5% w/v |
| | Water for injection to 100% | |
| (f) | Injection II | 10 mg/ml) |
| | Compound X | 1.0% w/v |
| | Sodium phosphate BP | 3.6% w/v |
| | 0.1N Sodium hydroxide solution | 15.0% v/v |
| | Water for injection to 100% | |
| (g) | Injection III | (1 mg/ml,buffered to pH6) |
| | Compound X | 0.1% w/v |
| | Sodium phosphate BP | 2.26% w/v |
| | Citric acid | 0.38% w/v |
| | Polyethylene glycol 400 | 3.5% w/v |
| | Water for injection to 100% | |

Note

The above formulations may be obtained by conventional procedures well known in the pharmaceutical art. The tablets (a)–(c) may be enteric coated by conventional means, for example to provide a coating of cellulose acetate phthalate.

What is claimed is:

1. A compound of the formula I:

(I)

wherein:

$R^1$ represents hydrogen or methoxy;

$R^2$ represents 2-methoxyethoxy, 3-methoxypropoxy, 2-ethoxyethoxy, trifluoromethoxy, 2,2,2-trifluoroethoxy, 2-hydroxyethoxy, 3-hydroxypropoxy, 2-(N,N-dimethylamino)ethoxy, 3-(N,N-dimethylamino)propoxy, 2-morpholinoethoxy, 3-morpholinopropoxy, 4-morpholinobutoxy, 2-piperidinoethoxy, 3-piperidinopropoxy, 4-piperidinobutoxy, 2-(piperazin-1-yl )ethoxy, 3-(piperazin-1-yl )propoxy, 4-(piperazin-1-yl)butoxy, 2-(4-methylpiperazin-1-yl)ethoxy, 3-(4-methylpiperazin-1-yl)propoxy or 4-(4-methylpiperazin-1-yl)butoxy;

the phenyl group bearing $(R^3)_2$ is selected from: 4-bromo-2-fluorophenyl, 2,4-difluorophenyl, 4-chloro-2-fluorophenyl, 2-fluoro-4-methylphenyl, 2-fluoro-4-methoxyphenyl and 4-cyano-2-fluorophenyl;

and salts thereof.

2. The compound as claimed in claim 1 wherein $R^1$ is methoxy.

3. The compound as claimed in claim 1 wherein the phenyl group bearing $(R^3)_2$ is 4-chloro-2-fluorophenyl or 4-bromo-2fluorophenyl.

4. The compound as claimed in claim 1 wherein $R^2$ is 2-methoxyethoxy, 3-methoxypropoxy, trifluoromethoxy, 2,2,2-trifluoroethoxy, 2-hydroxyethoxy, 3-hydroxypropoxy, 2-(N,N-dimethylamino)ethoxy, 3-(N,N-dimethylamino) propoxy, 2-morpholinoethoxy, 3-morpholinopropoxy, 2-piperidinoethoxy, 3-piperidinopropoxy, 2-(piperazin-1-yl) ethoxy, 3-(piperazin-1-yl)propoxy, 2-(4-methylpiperazin-1-yl)ethoxy, or 3-(4-methylpiperazin-1-yl)propoxy.

5. The claimed as claimed in claim 1 wherein $R^2$ is 2-methoxyethoxy, 2-morpholinoethoxy, 3-morpholinopropoxy or 2-(4-methylpiperazin-1-yl)ethoxy.

6. The compound as claimed in claim 5 wherein $R^2$ is 2-methoxyethoxy or 3-morpholinopropoxy.

7. A compound selected from the group consisting of:

4-(4-chloro-2-fluoroanilino)-6-methoxy-7-(2-methoxyethoxy)quinazoline;

4-(4-chloro-2-fluoroanilino)-6-methoxy-7-(2-morpholinoethoxy)quinazoline;

4-(4-chloro-2-fluoroanilino)-6-methoxy-7-(3-morpholinopropoxy)quinazoline;

4-(4-chloro-2-fluoroanilino)-6-methoxy-7-(2-(4-methylpiperazin-1-yl)-ethoxy)quinazoline;

4-(4-bromo-2-fluoroanilino)-6-methoxy-7-(3-morpholinoproxy)quinazoline;

and salts thereof.

8. A compound selected from the group consisting of:

4-(4-bromo-2-fluoroanilino)-6-methoxy-7-(2-methoxyethoxy)quinazoline;

4-(4-bromo-2fluoroanilino)-6-methoxy-7-(2-(4-methylpiperazin-1yl)ethoxy)quinazoline;

and salts thereof.

9. The compound as claimed in any one of claims 1, 7 and 8 in the form of a pharmaceutically acceptable salt.

10. A process for the preparation of a compoundf of formula I or salt thereof, as defined in claim 1, which comprises:

(a) the reaction of a compound of the formula III:

(III)

(wherein $R^1$ and $R^2$ are as defined in claim 1 and $L^1$ is a displaceable moiety) with a compound of the formula IV:

(IV)

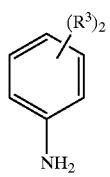

(wherein R³ is as defined in claim 1), whereby to obtain compounds of the formula I or salts thereof;

(b) the reaction of a compound of the formula VI:

(VI)

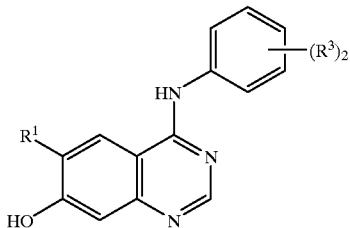

(wherein R¹ and R³ are as defined in claim 1) with a compound of formula VII:

R⁴—L¹    (VII)

(wherein L¹ is as defined herein and R⁴ is 2-methoxyethyl, 3-methoxypropyl, 2ethoxyethyl, trifluoromethyl, 2,2,2-trifluoroethyl, 2-hydroxyethyl, 3-hydroxypropyl, 2-(N,N-dimethylamino)ethyl, 3-(N,N-dimethylamino)propyl, 2-morpholinoethyl, 3-morpholinopropyl, 4-morpholinobutyl, 2-piperidinoethyl, 3-piperidinopropyl, 4-piperidinobutyl, 2-(piperazin-1-yl)ethyl, 3-(piperazin-1-yl)propyl, 4-(piperazin-1-yl)butyl, 2-(4-methylpiperazin-1-yl)ethyl, 3-(4-methylpiperazin-1-yl)propyl or 4-(4-methylpiperazin-1-yl)butyl);

(c) the reaction of a compound of the formula VIII:

(VIII)

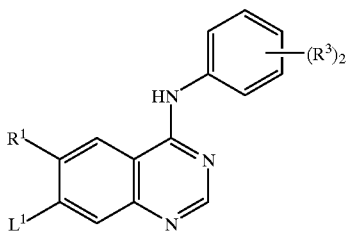

with a compound of the formula IX:

R²—H    (IX)

(wherein L¹ is as defined herein and R¹, R² and R³ are as defined in claim 1);

(d) for the preparation of compounds of formula I and salts thereof wherein R² is R⁵C$_{1-4}$alkoxy, (wherein R⁵ is selected from methoxy, ethoxy, hydroxy, N,N-dimethylamino, morpholino, piperidino, piperazin-1-yl or 4-methylpiperazin-1-yl), reacting a compound of the formula X:

(X)

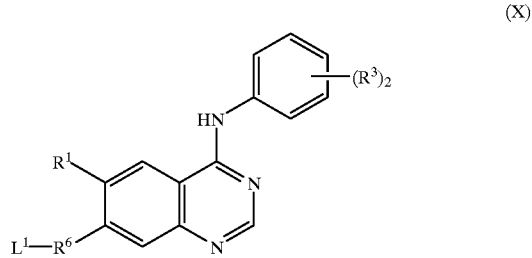

(wherein L¹ is as defined herein, R¹ and R³ are as defined in claim 1 and R⁶ is C$_{1-4}$alkoxy) with a compound of the formula XI:

R⁵—H    (XI)

(wherein R⁵ is as defined herein);

and when a salt of a compound of formula I is required, reaction of the compound obtained with an acid or base whereby to obtain the desired salt.

11. A pharmaceutical composition which comprises as active ingredient a compound of formula I or a pharmaceutically acceptable salt thereof as in any one of claims 1, 7 and 8 in association with a pharmaceutically le excipient or carrier.

12. A method for treating a disease condition mediated at least in part by angiogenesis and/or increased vascular permeability by producing an antiangiogenic and/or vascular permeability reducing effect in a warm-blooded animal, which comprises administering to said animal an effective amount of a compound of formula I or a pharmaceutically acceptable salt thereof as claimed in any one of claims 1, 7 and 8.

* * * * *